(12) United States Patent
Raymo et al.

(10) Patent No.: US 8,198,436 B2
(45) Date of Patent: Jun. 12, 2012

(54) COLORIMETRIC DETECTION OF CYANIDE WITH A CHROMOGENIC OXAZINE

(75) Inventors: Francisco M. Raymo, Coral Gables, FL (US); Massimiliano Tomasulo, Miami, FL (US)

(73) Assignee: The University of Miami, Miami, FL (US)

( * ) Notice: Subject to any disclaimer, the term of this patent is extended or adjusted under 35 U.S.C. 154(b) by 1106 days.

(21) Appl. No.: 11/991,355

(22) PCT Filed: Sep. 1, 2006

(86) PCT No.: PCT/US2006/034331
§ 371 (c)(1),
(2), (4) Date: Mar. 3, 2008

(87) PCT Pub. No.: WO2007/028080
PCT Pub. Date: Mar. 8, 2007

(65) Prior Publication Data
US 2009/0258429 A1    Oct. 15, 2009

Related U.S. Application Data

(60) Provisional application No. 60/712,900, filed on Sep. 1, 2005.

(51) Int. Cl.
*C07D 265/14* (2006.01)
*G01N 21/78* (2006.01)
(52) U.S. Cl. .............................. 544/89; 436/109; 422/50
(58) Field of Classification Search .................... 544/89; 436/109; 422/50
See application file for complete search history.

(56) References Cited

U.S. PATENT DOCUMENTS

| | | |
|---|---|---|
| 6,198,655 B1 | 3/2001 | Heath et al. |
| 7,790,068 B2 | 9/2010 | Raymo et al. |
| 2007/0221889 A1 | 9/2007 | Raymo et al. |
| 2008/0213625 A1 | 9/2008 | Raymo et al. |
| 2008/0305047 A1 | 12/2008 | Raymo et al. |
| 2009/0258429 A1 | 10/2009 | Raymo et al. |
| 2010/0112560 A1 | 5/2010 | Raymo et al. |
| 2010/0249403 A1 | 9/2010 | Tomasulo et al. |
| 2011/0095243 A1 | 4/2011 | Raymo et al. |

FOREIGN PATENT DOCUMENTS

| | | |
|---|---|---|
| WO | 2005/029033 A2 | 9/2004 |
| WO | 2006/110610 | 10/2006 |
| WO | 2008/018894 A2 | 2/2008 |

OTHER PUBLICATIONS

Raymo & Giordani. All-optical processing with molecular switches. (2002). 99: 8 4941-4944.*
Sackus et al., Khimiya Geterotsiklicheskikh Soedinenii (1989), (5), 672-6.*
Raymo & Giordani "All-optical processing with molecular switches" Proc. Natl. Acad. Sci. USA 99:4941-4944 (2002).
Badugu et al. "Cyanide-Sensitive Fluorescent Probes" *Dyes and Pigments*, Jan. 2005, vol. 64, pp. 49-55.
Badugu et al. "Enhanced Fluorescence Cyanide Detection at Physiologically Lethal Levels: Reduced ICT-Based Signal Transduction" *J. Am. Chem. Soc.*, Feb. 2005, vol. 127, pp. 3635-3641.
Badugu et al. "Excitation and Emission Wavelength Ratiometric Cyanide-Sensitive Probes for Physiological Sensing" *Analytical Biochemistry*, 2004, vol. 327, pp. 82-90.
Chow et al. "A Heterobimetallic Ruthenium (II)-Copper(II) Donor-Acceptor Complex as a Chemodosimetric Ensemble for Selective Cyandie Detection" *Inorganic Chemistry*, Nov. 2004, vol. 43, pp. 8387-8393.
Lu et al. "Vapor and Liquid Phase Detection of Cyanide on a Microchip" *Electrophoresis*, 2004, vol. 25, pp. 116-122.
Zheng et al. "Evaluation and Testing of Analytical Methods for Cyanide Species in Municipal and Industrial Contaminated Waters" *Environ. Sci. Technol.*, 2003, vol. 37, pp. 107-115.
International Search Report for Appln. No. PCT/US2006/034331 (completed 2006).
Written Opinion of the ISA for Appln. No. PCT/US2006/034331 (completed Nov. 13, 2006).
Raymo & Tomasulo "Fluorescence modulation with photochromic switches" J. Phys. Chem. A 109:7343-7352 (2005). Tomasulo et al. "Fast and stable photochromic oxazines" J. Org. Chem. 70:8180-8189 (2005) and 16 pages of supporting information.
Tomasulo et al. "A fast and stable photochromic switch based on the opening and closing of an oxazine ring" Org. Lett. 7:1109-1112 (2005) and two pages of supporting information.
Tomasulo & Raymo "Colorimetric detection of cyanide with a chromogenic oxazine" Org. Lett. 7:4633-4636 (2005) and one page of supporting information.
Tomasulo et al. "Chromogenic oxazines for cyanide detection" J. Org. Chem. 71:744-753 (2006) and 13 pages of supporting information.
International Preliminary Report on Patentability for PCT/US2006/034331 dated Mar. 13, 2008.

* cited by examiner

*Primary Examiner* — Kahsay T Habte
(74) *Attorney, Agent, or Firm* — Nixon & Vanderhye P.C.

(57) ABSTRACT

A chromogenic oxazine compound for the colorimetric detection of cyanide was designed. Indeed, the [1,3]oxazine ring of our compound opens to form a phenolate chromophore in response to cyanide. The heterocyclic com-pound may be comprised of fused benzooxazine and indoline rings:

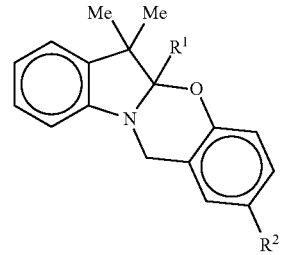

wherein $R^1$ is an alkyl (e.g., methyl, ethyl, propyl, isopropyl, butyl, isobutyl), a substituted alkyl, a cycloalkyl (e.g., cyclopentyl, cyclohexyl), a substituted cycloalkyl, an aryl (e.g., phenyl), or a substituted aryl and $R^2$ is a chromophore (e.g., nitroso, nitro, azo dyes). This quantitative chromogenic transformation permits the detection of micromolar concentrations of cyanide in water. Furthermore, our chromogenic oxazine is insensitive to the presence of large concentrations of fluoride, chloride, bromide or iodide anions, which are generally the principal interferents in the colorimetric detection of cyanide.

28 Claims, 25 Drawing Sheets

Figure 17A
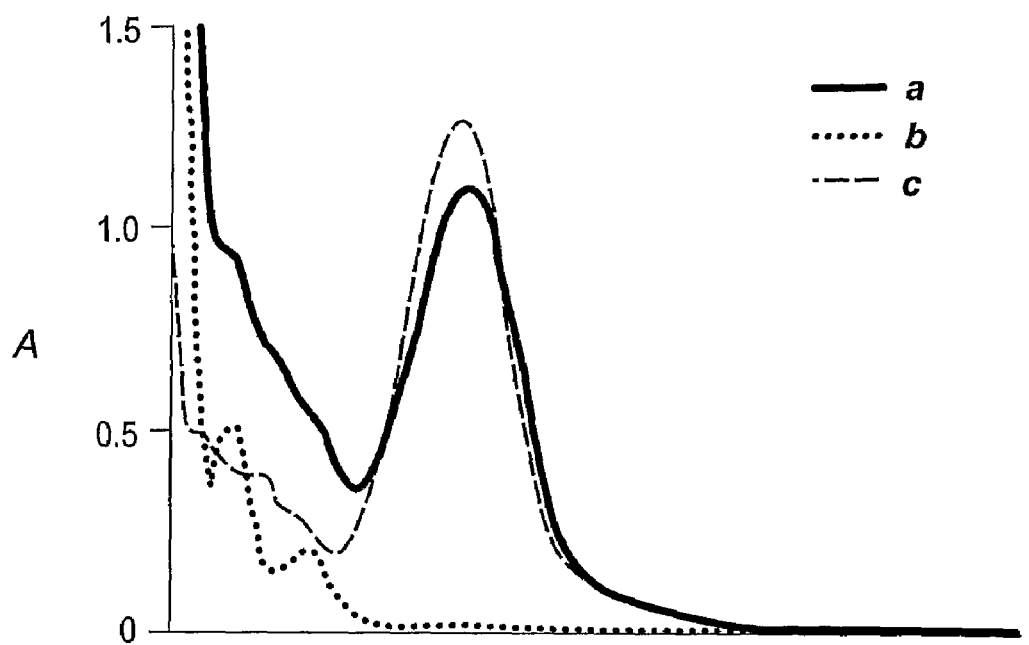
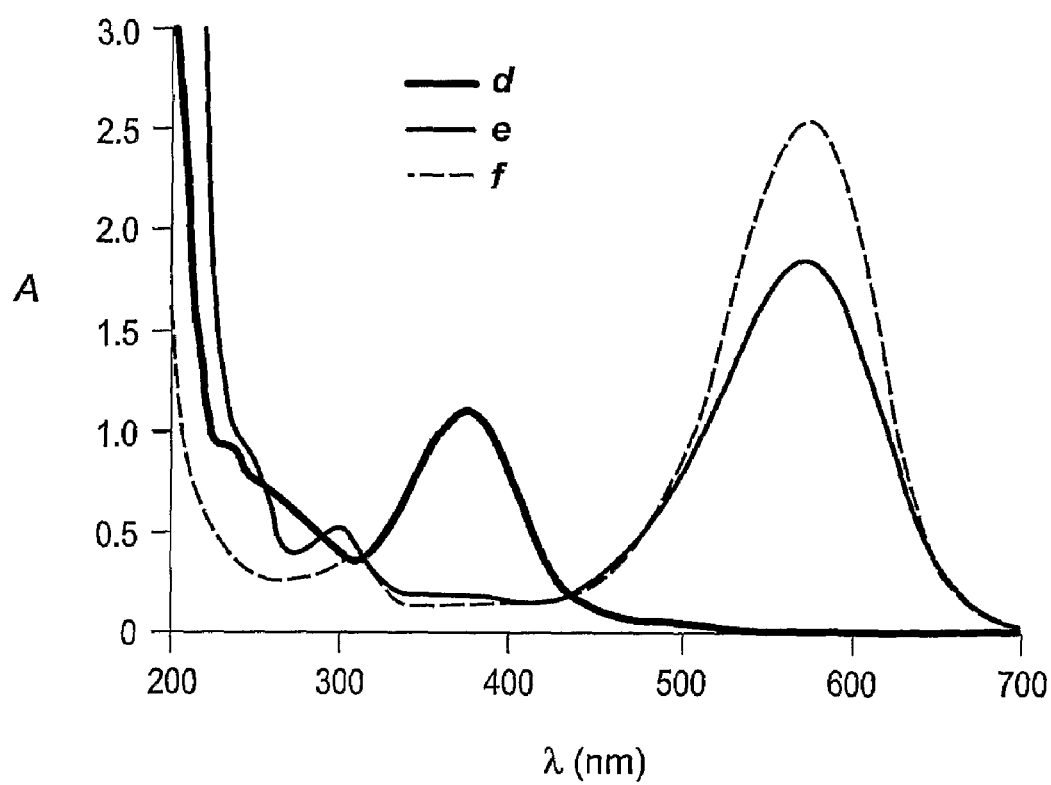
Figure 17B

Figure 19
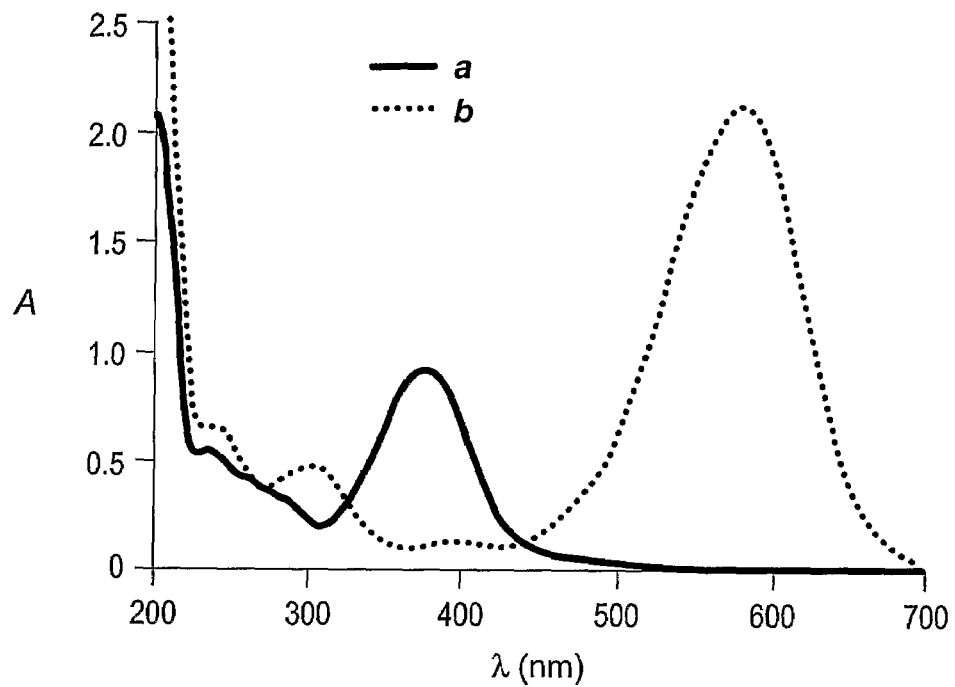
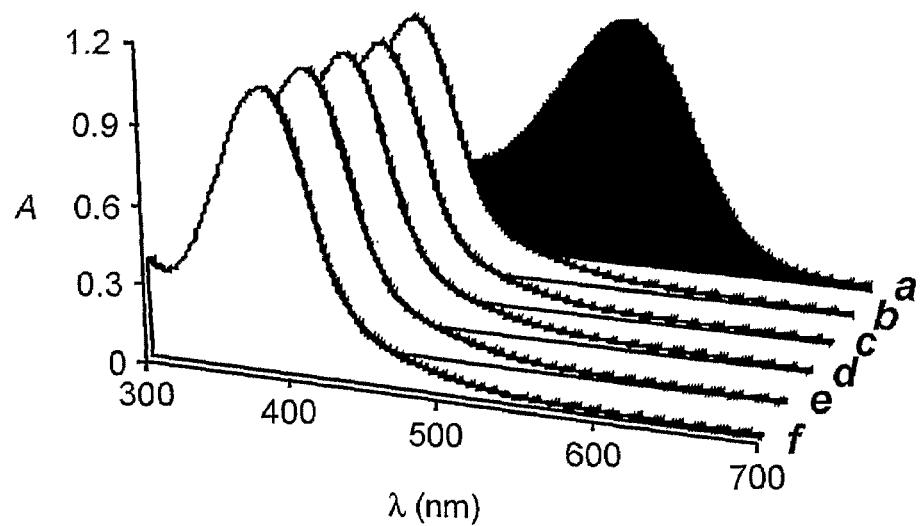
Figure 20

US 8,198,436 B2

COLORIMETRIC DETECTION OF CYANIDE WITH A CHROMOGENIC OXAZINE

CROSS REFERENCE TO RELATED APPLICATIONS

This is a national-stage application under 35 U.S.C. 371 of Int'l Application No. PCT/US2006/034331, filed Sep. 1, 2006. This application claims priority benefit of provisional U.S. Application No. 60/712, 900, filed Sep. 1, 2005. The entire contents of the aforementioned applications are incorporated by reference herein.

STATEMENT REGARDING FEDERALLY-SPONSORED RESEARCH

The U.S. Government has certain rights in this invention as provided for by the terms of CHE-0237578 awarded by the National Science Foundation.

BACKGROUND OF THE INVENTION

The invention relates to chromogenic oxazines useful for detection of cyanide.

The cyanide anion is a particularly strong nucleophile and forms stable complexes with a variety of transition metals in aqueous solution.[1-3] In fact, a wealth of diverse industrial applications have been developed around the excellent binding properties of this particular ligand.[4-5] The strong affinity of cyanide for transition metals, however, has deleterious consequences on cell metabolism.[6-8] Specifically, this anion binds the active site of cytochrome oxidase and inhibits the mitochondrial electron-transport chain. As a result, cyanide is extremely toxic and even relatively small amounts (e.g., 0.5-3.5 mg per kg of body weight) are lethal to humans.[9] Unfortunately, cyanide does not easily decompose in the environment.[10] Therefore, the accidental spillage of this toxic chemical from industrial plants, or even its intentional release, can contaminate drinking waters and become a serious threat to human health. Indeed, the concentration of cyanide in drinking water cannot be greater than 1.9 μM in accordance with the World Health Organization standard.[11]

Numerous standard methods for the detection of micromolar amounts cyanide in water have been developed relying on a diversity of experimental protocols and detection techniques.[12] Most of such strategies, however, require either multistep procedures with tedious sample pretreatments or sophisticated instrumentation. The development of chemosensors[13-18] for the recognition of anions[17-31] can facilitate the qualitative, and perhaps even the quantitative, determination of cyanide. In particular, the identification of chromogenic compounds that respond to the presence of cyanide anions with fast and visible color changes would offer the opportunity to screen rapidly water samples relying exclusively on the naked eye. Indeed, a few organic molecules and transition metal complexes able to signal the presence of cyanide with pronounced changes in their absorption and emission properties have been identified.[32-37] Their operating principles are based on hydrogen bonding interactions, metal coordination, or the formation of covalent bonds between the nucleophilic cyanide anion and compatible electrophilic centers. Some of the chemosensors can even detect micromolar amounts of cyanide.[36-37] But most of them suffer from the deleterious interference of other anions.[32-37] Halide anions in particular, and especially fluoride, tend to mask the response of cyanide of such chemosensors.[32,34b,35,37c]

The present invention is directed to improved detection of cyanide that addresses the aforementioned problems by designing heterocyclic compounds for the calorimetric detection of cyanide. The skeleton of our molecules fuses a benzooxazine ring to an indoline fragment and can be efficiently synthesized from readily available precursors. In the presence of cyanide, our molecules are converted into cyanoamines with the concomitant appearance of an intense band in the visible region of the absorption spectrum. The developing absorption is a result of the opening of the benzooxazine ring with the formation of a phenolate chromophore. Nuclear magnetic resonance spectroscopy and X-ray crystallographic analyses demonstrate that the covalent attachment of a cyanide anion to the indoline fragment is responsible for this transformation. The chromogenic process is particularly fast for the methyl-substituted oxazine and can be exploited to detect micromolar concentrations of cyanide in water. Furthermore, the calorimetric response of our compounds to cyanide does not suffer the interference of the halide anions, which instead are known to complicate the detection of cyanide in conventional sensing protocols. Thus, our mechanism and compounds for the colorimetric identification of cyanide can lead to the development of practical strategies for the convenient determination of this toxic anion in aqueous environments.

Compounds, compositions, articles (e.g., test kits or single-use devices), and processes for using and making the aforementioned products are provided. Other advantages and improvements are described below or would be apparent from the disclosure herein.

SUMMARY OF THE INVENTION

The invention is used to detect cyanide using a chromogenic oxazine. A reagent for colorimetric detection of cyanide is comprised of one or more oxazine compounds. They are preferably described as comprised of a skeleton of fused benzooxazine and indoline rings such as, for example:

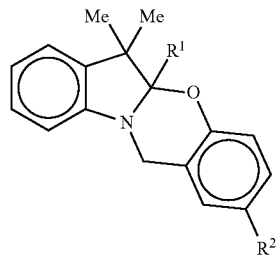

wherein $R^1$ is an alkyl (e.g., methyl, ethyl, propyl, isopropyl, butyl, isobutyl), a substituted alkyl, a cycloalkyl (e.g., cyclopentyl, cyclohexyl), a substituted cycloalkyl, an aryl (e.g., phenyl), or a substituted aryl and $R^2$ is a chromophore (e.g., nitroso, nitro, azo dyes). $R^1$ is preferably methyl and $R^2$ is preferably nitrophenylazo (not nitro), but any oxazine that is capable of being cleaved by cyanide to form a phenolate chromophore can be used. A specific example of the oxazine compound is 2-(4'-nitrophenylazo)-5a,6,6-trimethyl-5a,6-dihydro-12H-indolo[2,1-b][1,3]benzooxazine.

A process for detecting cyanide is provided. A sample may be subjected to further processing prior to detection that improves at least sensitivity or specificity for cyanide. Also provided are processes for using and making these products. It should be noted, however, that a claim directed to the product is not necessarily limited to these processes unless the particular steps of the process are recited in the product claim.

Further aspects of the invention will be apparent to a person skilled in the art from the following description of specific embodiments and the claims, and generalizations thereto.

BRIEF DESCRIPTION OF THE DRAWINGS

FIG. 3 is a schematic of the synthesis of the [1,3]oxazines 7a and 8a.

FIG. 5A illustrates a first structure (I) of two crystallographically-independent molecules present in the crystals of 7a.

FIG. 6A illustrates a second structure (II) of two crystallographically-independent molecules present in the crystals of 7a.

FIG. 8A illustrates the single-crystal X-ray structure of 8a.

FIGS. 17A and 17B show steady-state absorption spectra (0.1 mM, MeCN, 298 K) of 8a (a), 10 (b), 11 (c), 7a before (d) or after (e) the addition of $Bu_4NOH$ (100 eq.), or 12 (f).

FIG. 19 shows steady-state absorption spectra (0.1 mM, MeCN, 298 K) of 8a before (a) or after (b) the addition of $Bu_4NCN$ (35 eq.).

FIG. 20 shows steady-state absorption spectra (0.1 mM, 550 μL, MeCN, 298 K) of 7a after the addition of sodium phosphate buffer (550 μL, pH 7.6) without (b) or with 10 mM of NaCN (a), NaF (c), NaCl (d), NaBr (e), or NaI (f).

DESCRIPTION OF SPECIFIC EMBODIMENTS OF THE INVENTION

Figure 1:
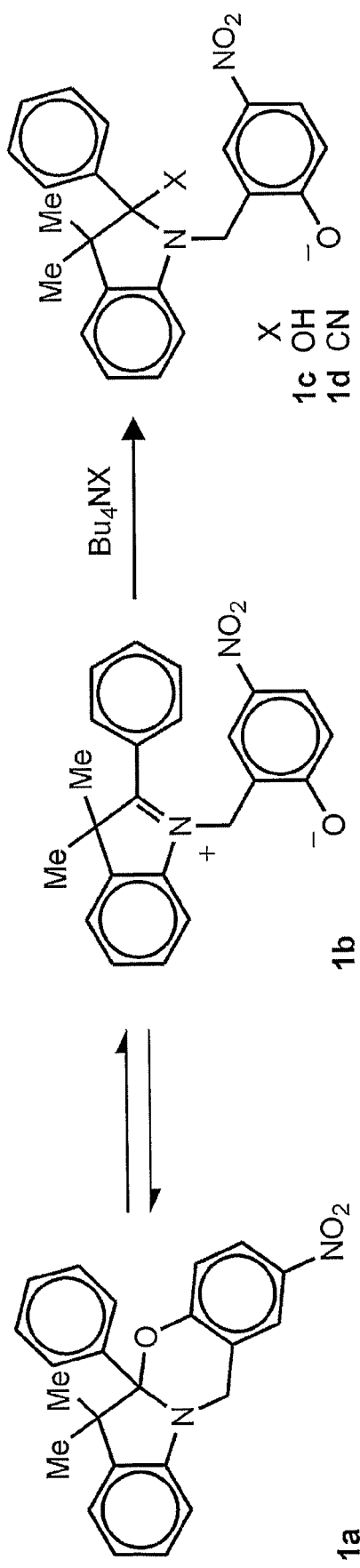
FIG. 1 is a schematic of the transformation of the [1,3] oxazine 1a into either the hemiaminal 1c or the cyanoamine 1d.

In one embodiment of the invention, a chromogenic compound of the formula is provided:

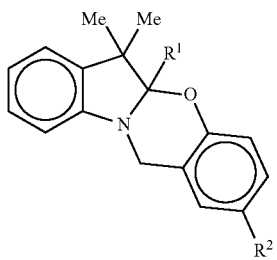

wherein $R^1$ is an alkyl (e.g., methyl, ethyl, propyl, isopropyl, butyl, isobutyl), a substituted alkyl, a cycloalkyl (e.g., cyclopentyl, cyclohexyl), a substituted cycloalkyl, an aryl (e.g., phenyl), or a substituted aryl and $R^2$ is a chromophore (e.g., nitroso, nitro, azo dyes). $R^1$ is preferably methyl and $R^2$ is preferably nitrophenylazo (not nitro), but any oxazine that is capable of being cleaved by cyanide to form a phenolate chromophore can be used. A specific example of the oxazine compound is 2-(4'-nitrophenylazo)-5a,6,6-trimethyl-5a,6-dihydro-12H-indolo[2,1-b][1,3]benzooxazine.

A solution comprising one or more of the compounds may be provided, wherein the compound(s) is soluble in the solution. The solution may contain an organic solvent (e.g., aliphatic hydrocarbons, aromatic hydrocarbons, halogenated aliphatic hydrocarbons, halogenated aromatic hydrocarbons, or any mixture thereof). Alternatively, the solution may contain water.

A two-phase system may also be provided, which is comprised of immiscible organic and aqueous phases, wherein the system further comprises one or more of the compounds and at least one phase-transfer catalyst (PTC). The immiscible organic and aqueous phases may be mixed in the presence of a PTC to cleave chromogen by cyanide to form chromophore. The PTC may be a quaternary ammonium salt, a phosphonium salt, a crown ether, or a polyalkyleneglycol. The compound(s) is preferably soluble in the organic phase. The organic phase may be an aliphatic hydrocarbon, an aromatic hydrocarbon, a halogenated aliphatic hydrocarbon, a halogenated aromatic hydrocarbon, or any mixture thereof. Cyanide is preferably dissolved at an alkaline pH in the aqueous phase.

A kit may be provided comprised of one or more containers in a package with one or more of the compounds in container(s) and optionally one or more of (i) an organic or aqueous solvent, (ii) a phase-transfer catalyst, and (iii) a calibration standard of a known amount(s) of cyanide (e.g., about 0.1 µM, less than about 1 µM, from about 1 µM to about 10 µM, from about 1 mM to about 10 mM) in a container(s). A solution, a system, or parts thereof may be in a container(s) or may be made from components therein. Other optional components of the kit includes (iv) a transfer pipet, (v) a reaction vessel (e.g., transparent multiwell plate, vial), (vi) a means for sampling, and (vii) written instructions for performing the assay. One test, at least three tests, or at least ten tests may be performed with the reagents packaged in the kit. A light- and moisture-resistant wrapper may be used for long-term storage of the kit.

A device may further be provided which is comprised of a reaction cell, wherein a sample which might contain cyanide is contacted with at least one of the compounds, solutions, or systems; a source which transmits light to the reaction cell; and a detector of light received from the reaction cell. A commercial spectrophotometer may be used or adapted for use. The device may be further comprised of a network of fluid transfer lines which dispenses a first fixed amount of the compound, solution, or system into the reaction cell; dispenses a second fixed amount of the sample into the reaction cell; and empties the reaction cell in each reaction cycle.

Alternatively, the device may be designed for a single use and disposed after contact with a sample. For example, one or more sites (e.g., pads, strips, wells) having a dry or wet chemical reservoir(s) on a support (e.g., dipstick to test liquid samples or wipe to test solid samples) may have at least one of the com-pounds, solutions, or systems in the reservoir(s). The reservoir's contents and the sample are brought into contact for field testing. If both are liquid, then they can be mixed; but if one is solid, then it is preferred that the other is liquid so that one can be wetted in the other. A clear or neutral-colored support is preferred such that development of the chromogenic reaction is distinguishable from the background. On the support, the application site(s) for a sample may be the same or different from the site(s) at which the reservoir(s) is located. The support may be a solid or semi-permeable matrix (e.g., cellulose, glass, metals, plastics); but it is preferably chemically nonreactive and may be porous to facilitate mixing between liquids or dissolving of a solid. Visual inspection of a reaction site will detect at least the presence of cyanide by a change in color, or the quantity of cyanide by comparing the developed color to a graduated color scale correlated to known amounts of cyanide. One single-use device, at least three single-use devices, or at least ten single-use devices may be packaged together. A light- and moisture-resistant wrapper may be used for long-term storage of the device(s).

At least one of the compounds, solutions, systems, kits, or devices may be used to detect and/or to quantify cyanide.

At least one of the compounds, solutions, systems, kits, or devices may be synthesized or manufactured by the skilled artisan in accordance with the description herein.

A method of detecting or quantifying cyanide is provided comprising (a) contacting a sample which might contain cyanide with at least one chromogen, wherein cyanide cleaves chromogen to form chromophore; (b) measuring light absorption by chromogen and/or chromophore; and (c) correlating a decrease in light absorption by the chromogen and/or an increase in light absorption by the chromophore with the presence of cyanide for detection or quantification.

The light absorption by chromogen may be measured at one or more wavelengths from about 360 nm to about 400 nm. The light absorption by chromophore may be measured at one or more wavelengths from about 560 nm to about 600 nm. The difference between wavelengths for maximum light absorption by a chromogen and a chromophore may be at least about 125 nm, at least about 150 nm, at least about 175 nm, or at least about 200 nm.

For a fixed amount or concentration of compound, light absorbance or transmission may be measured at one or more wavelengths. A blank sample containing a diluent (for a liquid sample) or an eluent (for a solid sample) may serve as a negative control (e.g., to subtract background from test samples). Known quantities of cyanide may serve as positive controls (e.g., a standard for confirming sensitivity to the presence of cyanide or calibrating the quantitation of an amount or concentration of cyanide in a sample). Varying the quantity (e.g., amount or concentration) of a compound may have a different range of cyanide quantities that can be determined. The effects of contaminants that might interfere with measurement of cyanide can be determined by comparing samples which do or do not contain the contaminant. For example, cleavage of chromogen by cyanide present in a sample to form chromophore (i.e., the compound reactive conversion) is not significantly inhibited by 10 mM of halide anions.

In an assay, absorbance or transmission at one or more wavelengths may be measured and correlated with the presence of cyanide in a sample. Sensitivity of the assay for cyanide may be measured by performing a dilution series of a known quantity of cyanide and determining the minimal amount or concentration that will be reliably detected under test conditions. It is preferred that the assay be sufficiently sensitive to measure 0.1 µM, 0.5 µM, 1 µM, or 5 µM of cyanide anion. For example, the ratio between the amounts of light absorbed by chromogen and chromophore may be calculated in a ratiometric assay and related to the quantity of cyanide in a sample. A liquid suspected of containing cyanide may be put into a diluent, or concentrated by evaporation or reverse osmosis prior to assay. The chemical reaction is then performed by mixing the liquid sample with the other components of the reaction. A solid that is suspected of containing cyanide may be "sampled" by applying a compound to the solid's exterior, exposing an internal surface of the solid and applying a compound to the exposed surface, soaking the solid in eluent to extract at least some cyanide that might be present, or treating chips or a powder of the solid as one would a liquid because cyanide is extracted into diluent rapidly due to the increased surface-to-volume ratio resulting from the decrease in the solid's size.

One or more compounds in an appropriate reaction cocktail may detect the presence of cyanide in a solid sample by painting the cocktail on the solid's exterior and allowing the reaction to develop a change in color. But the exterior of a solid might not be representative of the sample because of exposure to the environment (e.g., rain, soil, sun, sea) or preservative coating (e.g., paint, resin, sealants). In such situations, the exterior may be cleaned (e.g., with a solution containing surfactants and/or solvents), an internal surface may be exposed (e.g., boring with a drill, sanding with an abrasive, shaving with a knife), or the solid may be made into chips or a powder. A thus processed solid may then be sampled as described above.

Design and Synthesis. The [1,3]oxazine 1a (FIG. 1) is converted quantitatively 32 into the hemiaminal 1c upon treatment with Bu$_4$NOH in acetonitrile.[38] Nucleophilic attack of the hydroxide anion of Bu$_4$NOH to the indolium cation of the short-lived intermediate 1b is responsible for this transformation. Interestingly, the bimolecular conversion of 1a into 1c is accompanied by the appearance of a yellowish color. Indeed, the absorption spectrum of 1a shows bands in the ultraviolet region only, while the 4-nitrophenolate chromophore of 1c has an intense absorption centered at 440 nm.

Figure 2:
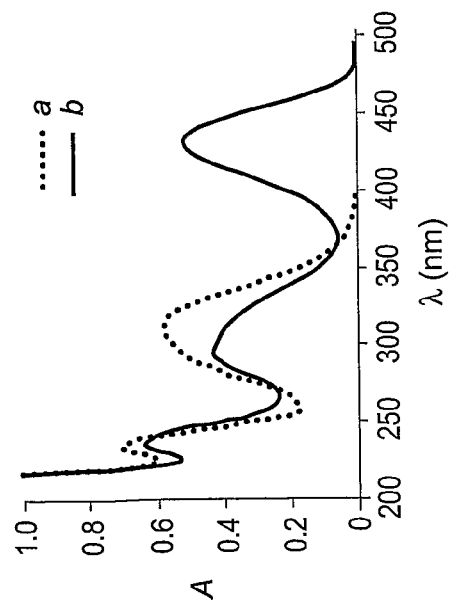
FIG. 2 shows steady-state absorption spectra (0.1 mM, MeCN, 298 K) of 1a before (a) and after (b) the addition of $Bu_4NCN$ (100 eq.).
Figure 3:
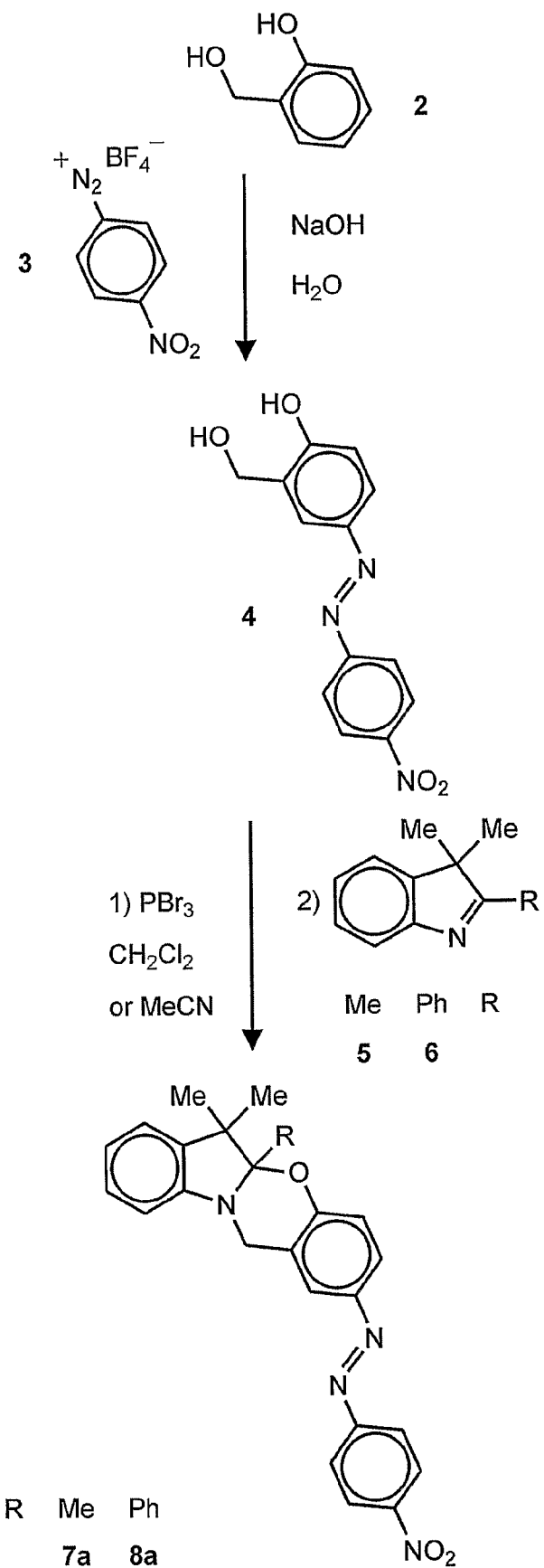

On the basis of these observations, we evaluated the response of 1a to Bu$_4$NCN under otherwise identical conditions. Once again, the characteristic band of a 4-nitrophenolate chromophore appears in the visible region of the absorption spectrum (a and b in FIG. 2) after the addition of the nucleophile. Thus, the cyanide anion can also react with the intermediate 1b and trap its 4-nitrophenolate chromophore in the form of the cyanoamine 1d (FIG. 1) with the concomitant appearance of color. It follows that similar transformations can be a possible operating mechanism for the colorimetric detection of cyanide by other oxazines. In this context, we designed the two compounds 7a and 8a (FIG. 3). They share a central [1,3]oxazine ring with 1a, but incorporate a 4-nitrophenylazo appendage in place of the nitro group. After ring opening and nucleophilic trapping, the extended conjugation of the resulting 4-nitrophenylazophenolate chromophore should translate into an enhancement of about 18 mM$^{-1}$cm$^{-1}$ in its molar extinction coefficient as compared to the 4-nitrophenolate chromophore of 1c. Therefore, 7a and 8a should be more appropriate than 1a as potential chromogenic probes for cyanide.

We synthesized the [1,3]oxazines 7a and 8a in two steps (FIG. 3) starting from 2-hydroxymethylphenol (2) and 4-nitrobenzenediazonium tetrafluoroborate (3).[39] The reaction of 2 and 3 in aqueous NaOH produces the 4-nitrophenylazophenol 4 in a yield of 96%. The treatment of 4 with PBr$_3$ and the reaction of the resulting bromide with an excess of the indole 5 or 6 in situ gives the corresponding [1,3]oxazine 7a or 8a in a yield of 41% or 51%, respectively.

Figure 4A:
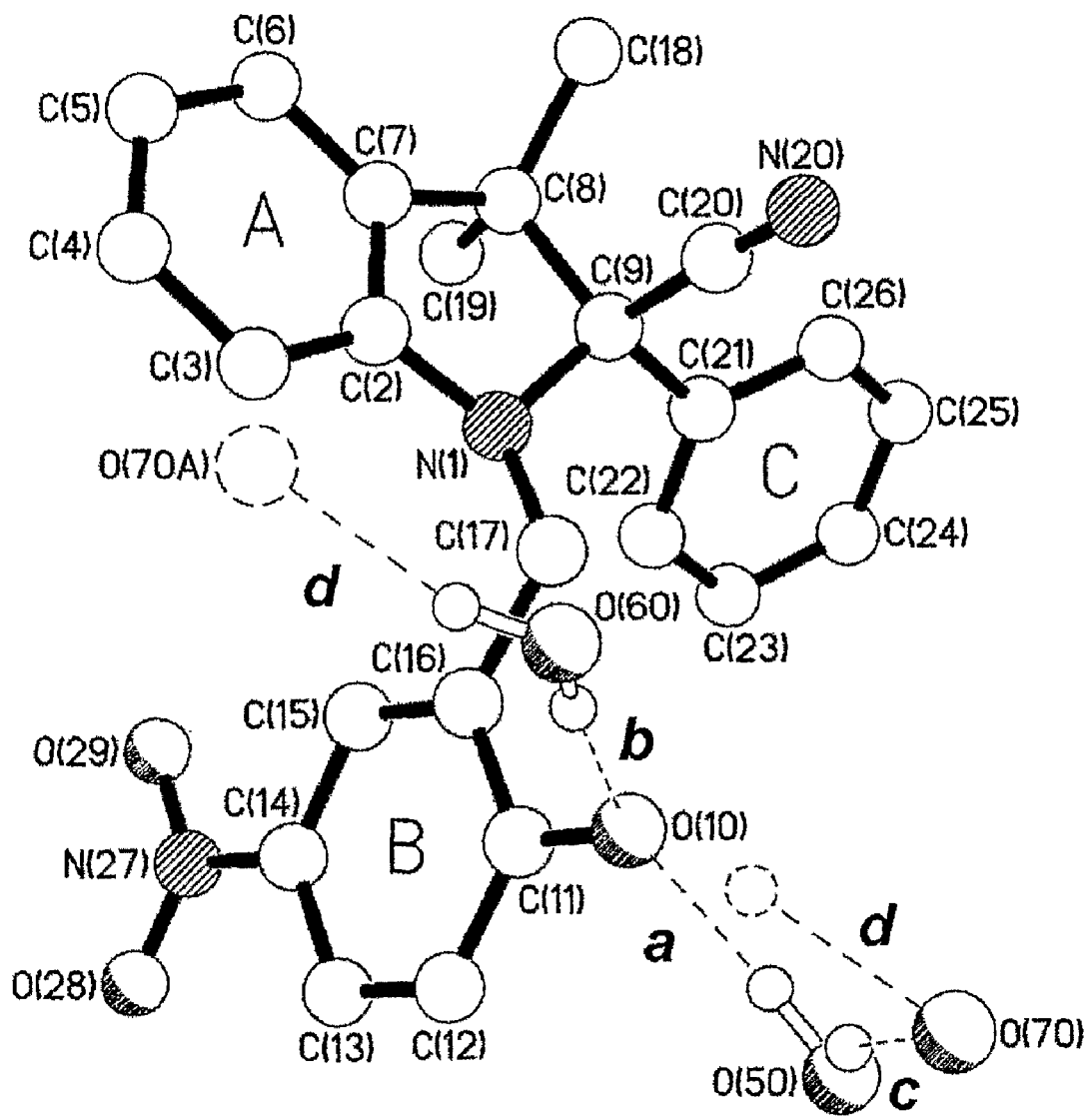
FIG. 4A illustrates the single-crystal X-ray structure of 1d (cation not depicted) showing the O—H . . . O hydrogen bonding interactions between the phenolate anion and the included solvent water molecules. The O—H . . . O hydrogen bonding geometries, [O . . . O], [H . . . O] (Å) and [O—H . . . ] (°), are (a) 2.718(4), 1.83, 167; (b) 2.719 (4), 1.83, 172; (c) 2.771 (5), 1.92, 158; (d) 2.742(5), 1.87, 163.
Figure 4B:
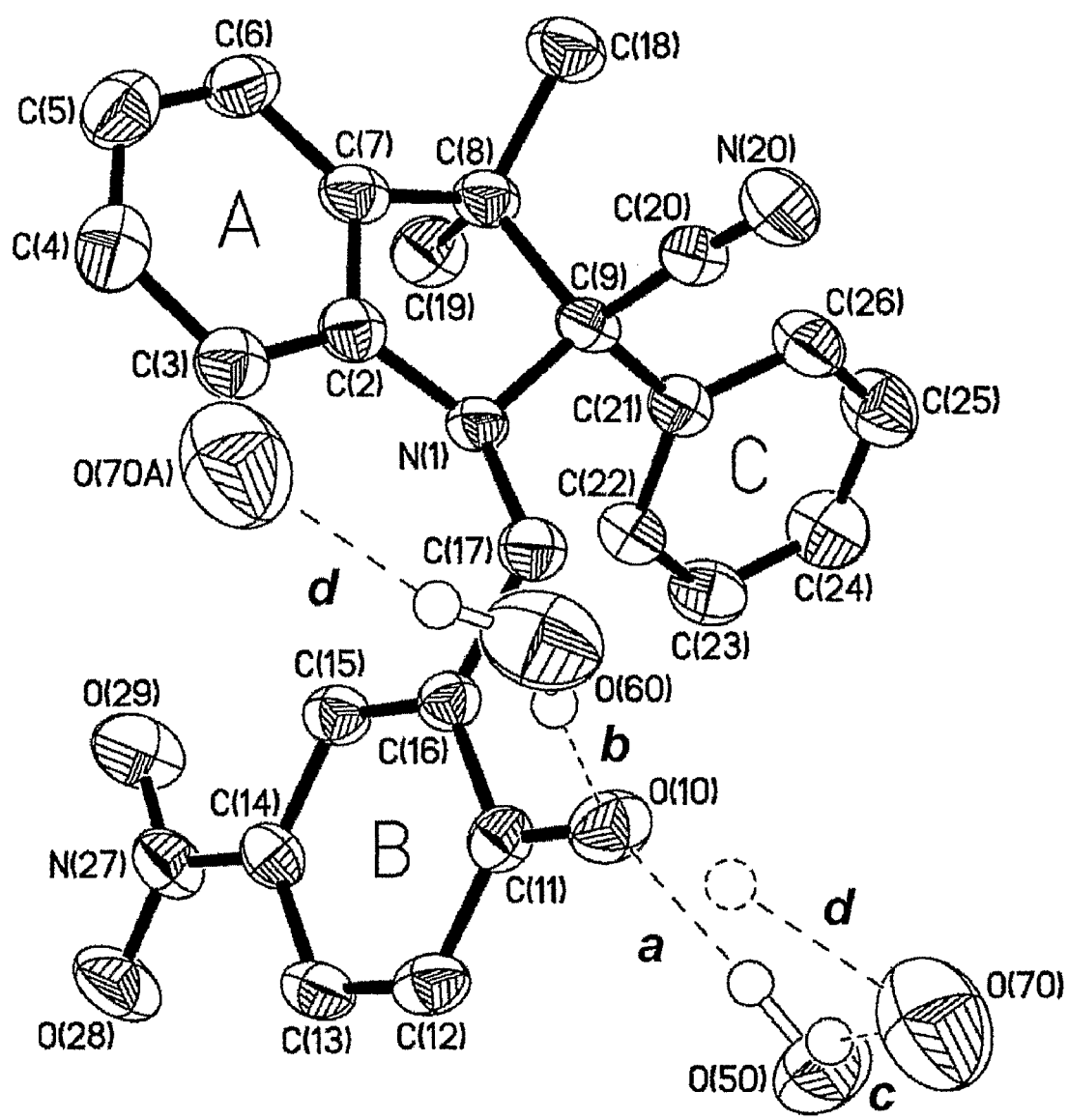
FIG. 4B illustrates the single-crystal X-ray structure of 1d showing 50% probability ellipsoids.

X-Ray Crystallography. The X-ray analysis of crystals of the cyanoamine 1d confirmed the opening of the benzooxazine ring with the addition of a cyano group (FIG. 4). The structure is somewhat similar to that of the hemiaminal 1c,[38b] including the incorporation of water molecules hydrogen bonded to the phenolate anion. The indoline ring of 1d has an envelope-type geometry, C(9) lying about 0.46 Å out of the {N(1) to C(8)} plane, which is coplanar to within about 0.02 Å. The geometry at N(1) is similar to that seen in related species,[38b] the nitrogen center being pyramidal (about 0.33 Å out of the plane of its substituents), and with its 2p$_z$ orbital approximately co-linear with the σ orbital of the C(9)-C(20) bond [the C(20)-C(9)-N(1)-lone pair dihedral angle is about 13°].

As can readily be seen from FIG. 4, the packing in the crystals of 1d is dominated by O—H . . . O hydrogen bonds involving the phenolate anion and the three included water molecules. There are also some notable cation . . . anion contacts with both rings A and B approached by methylene protons from the tetra-n-butylammonium cation [H . . . A 2.95 Å, C—H . . . A 178°; H . . . B 2.78 Å, C—H . . . B 175°]. The opposite faces of both of these rings are involved in a bifurcated C—H . . . π hydrogen bond from a methyl proton of the cation [H . . . A 3.28 Å, C—H . . . A 119°; H . . . B 3.15 Å, C—H . . . B 129°], the angles subtended at each ring centroid being about 155 and 172° for A and B, respectively. Ring C is not involved in any noteworthy intermolecular contacts.

In the structure of 1d, whilst the hydrate protons on O(50) and O(60) were located from ΔF maps, those on O(70) were not. This may be due to O(70) not appearing to act as a donor for any O—H . . . X hydrogen bonds, though it clearly acts as an acceptor for O—H . . . O interactions from O(50) and O(60); the closest heteroatom "approach" to O(70), other than the hydrogen bonds to O(50) and O(60), is about 3.82 Å from a C(12) carbon atom.

Figure 5A:
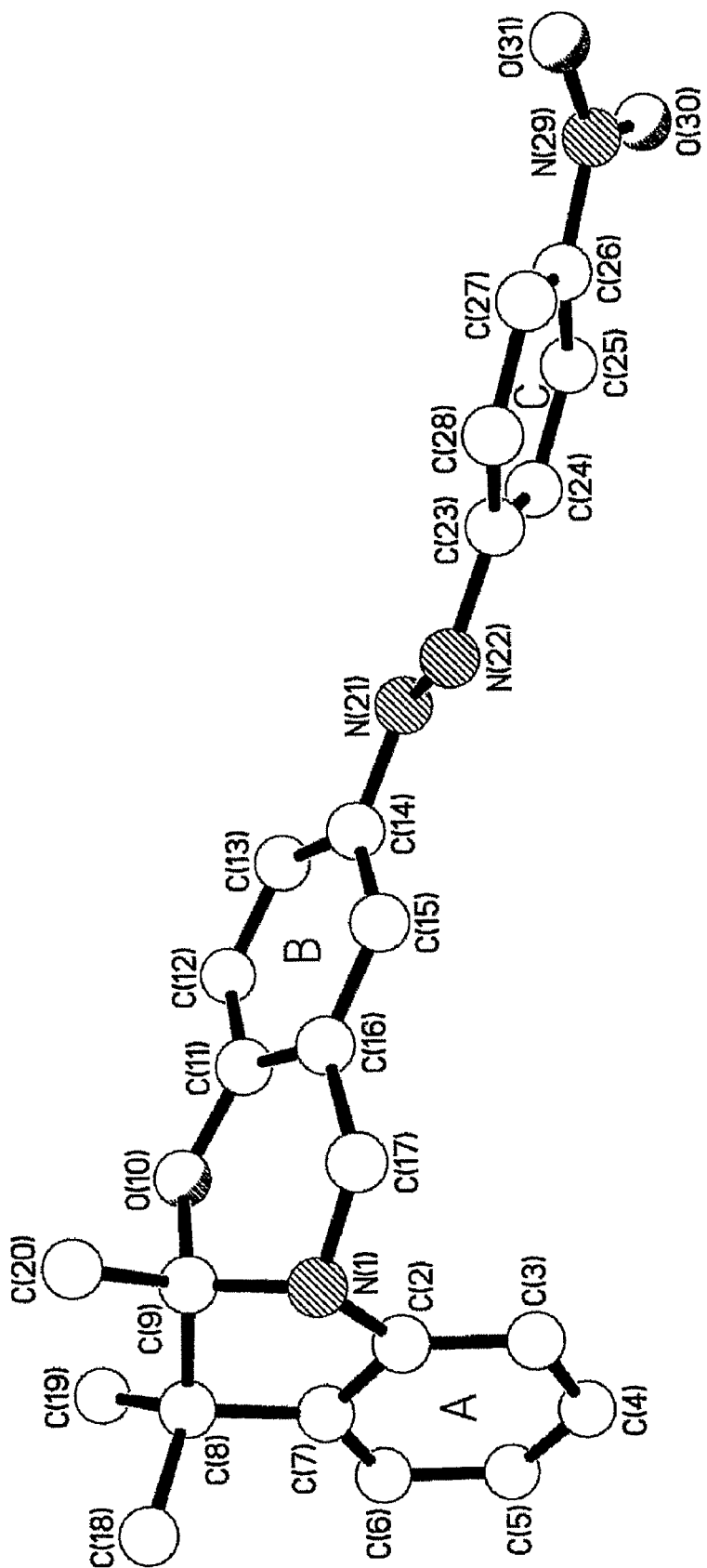
Figure 5B:
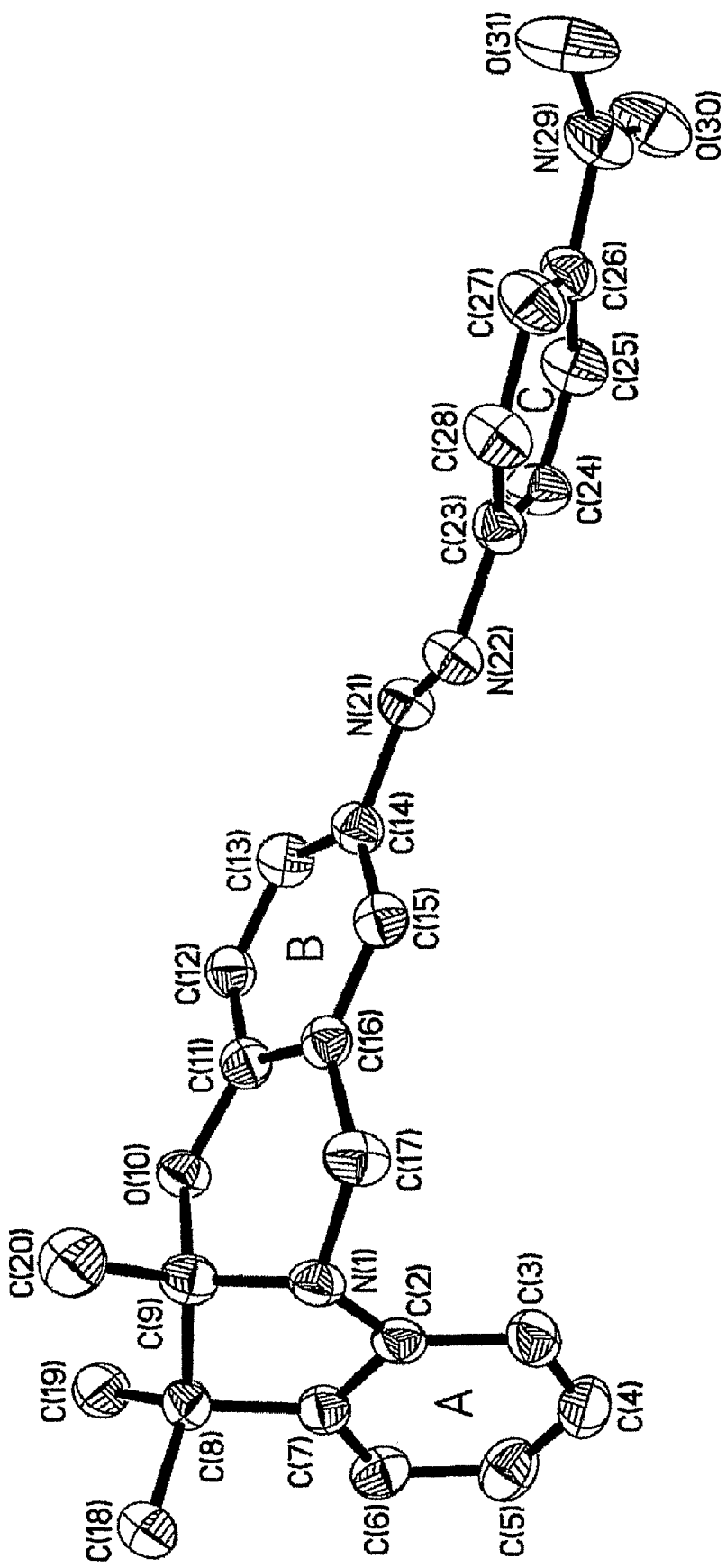
FIG. 5B illustrates structure (I) showing 50% probability ellipsoids.
Figure 6A:
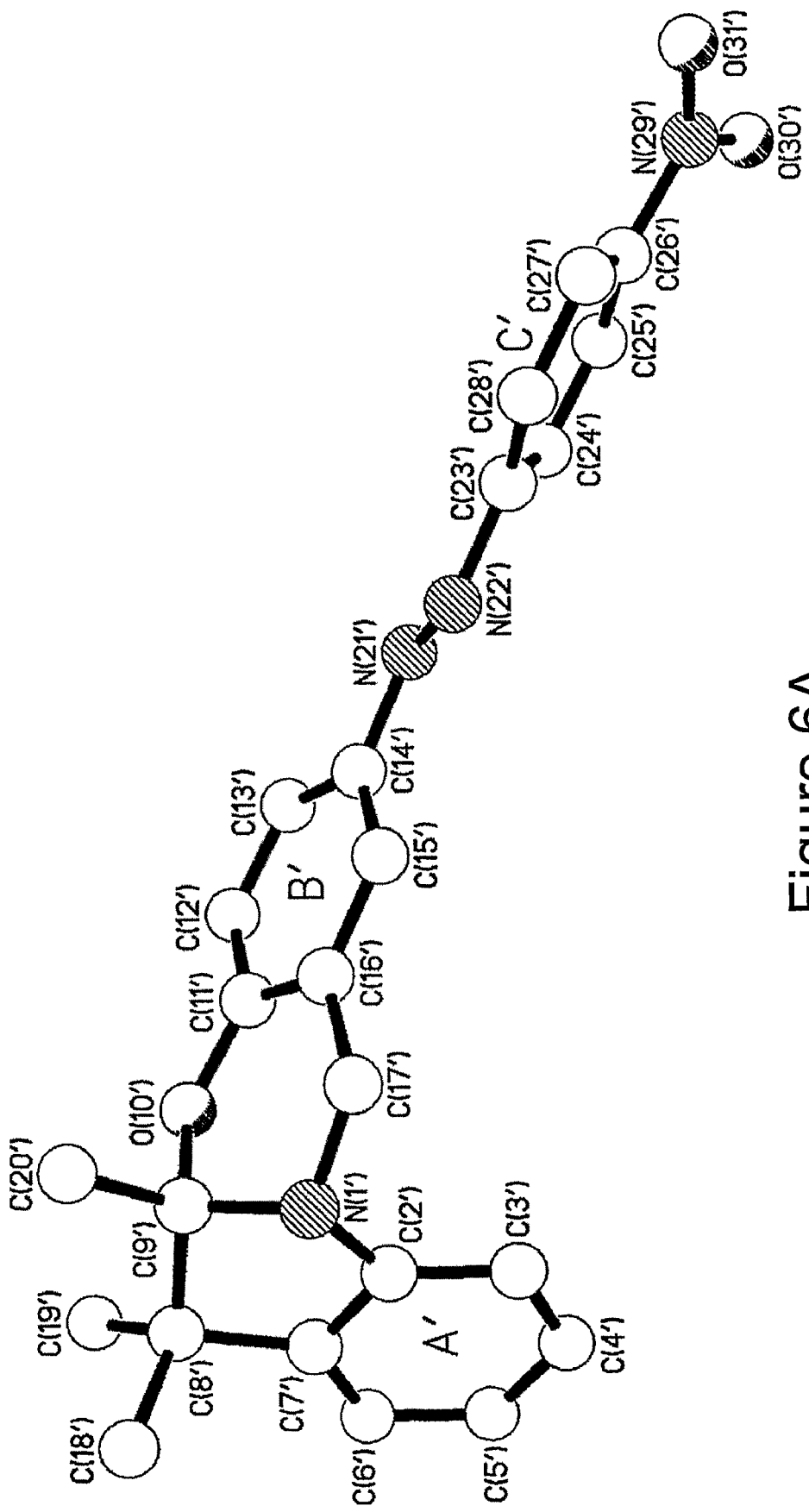
Figure 6B:
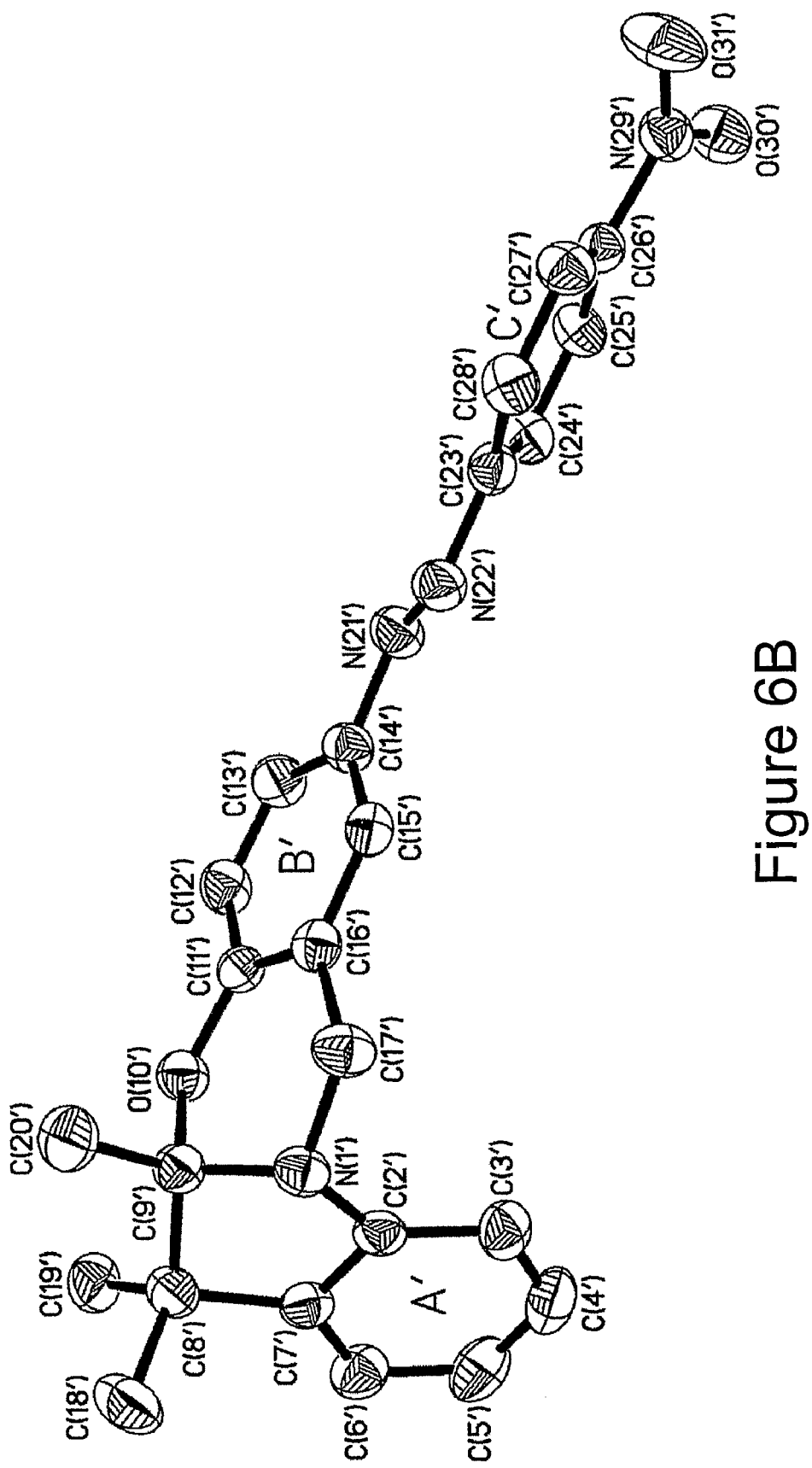
FIG. 6B illustrates structure (II) showing 50% probability ellipsoids.
Figure 7:
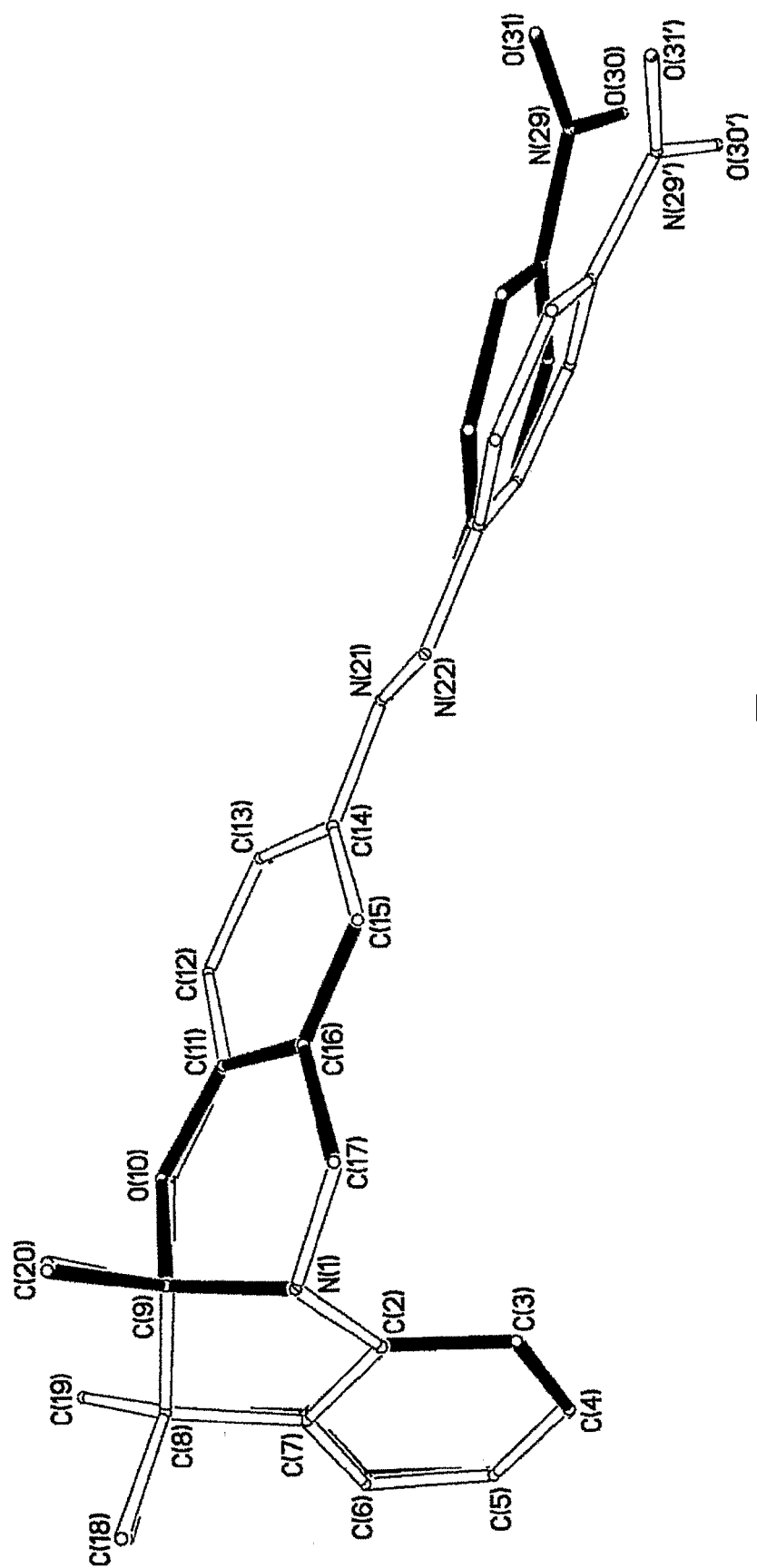
FIG. 7 illustrates superimposition of the two crystallographically-independent molecules (I and II) present in the crystals of 7a, showing the difference in conformation of the p-nitrophenyl moieties (I is drawn with filled bonds, II is drawn with open bonds). The N(1) to N(22) portions of the two independent molecules have a root mean square fit of about 0.048 Å.

The X-ray analysis of crystals of 7a revealed the presence of two independent molecules I and II (see FIGS. 5-6 for illustrations of molecules I and II, respectively). With the exception of the terminal p-nitrophenyl substituents, the two molecules have very similar conformations (FIG. 7), the N(1) to N(22) portions of the two independent molecules having a root mean square fit of about 0.048 Å. In common with 1a,[38b] both independent molecules have the expected near-orthogonal relationship between their indoline and benzooxazine ring systems (about 86° in both molecules). The indoline ring in each independent molecule has a similar envelope-type geometry to that seen in 1a [C(9) is about 0.46 Å out of the {N(1) to C(8)} plane, which is coplanar to within about 0.04 Å in I; C(9') is about 0.51 Å out of the {N(1') to C(8')} plane, which is coplanar to within about 0.02 Å in II]. Contrasting with 1a,[38b] their benzooxazine rings are more distorted. In 1a, the ring had an envelope-type geometry with N(1) lying about 0.53 Å out of the plane of the remaining C$_8$O atoms, which were coplanar to within about 0.08 Å. But in 7a both independent molecules have twisted benzooxazine rings with, for I, N(1) lying about 0.50 Å "below" and C(9) about 0.22 Å "above" the plane of the remaining C$_7$O atoms, which are coplanar to within about 0.08 Å (for II the values are 0.42 Å, 0.30 Å, and 0.06 Å, respectively). If the benzooxazine ring in 1a is viewed as twisted in a similar fashion, then N(1) lies about 0.48 Å "below" and C(9) about 0.14 Å "above" the plane of the remaining C$_7$O atoms which are coplanar to within about 0.04 Å. In each independent molecule, the N(1) nitrogen centers have pyramidal geometries, the nitrogen lying about 0.36 Å out of the plane of its substituents in both I and II. As was seen in 1a, here in both independent molecules of 7a the nitrogen 2p$_z$ orbital is approximately co-linear with the a orbital of the C(9)-O(10) bond, the O(10)—C(9)-N(1)-lone pair dihedral angles being about 8° and 7° in I and II, respectively. Though flat (with {C(14), N(21), N(22), C(23)} being coplanar to within 0.01 Å [0.01 Å]), the plane of the N$_2$ moiety is twisted with respect to ring B by about 16° [180], and to ring C by about 29° [21°]; these twists are in the same sense so that ring C is twisted by about 46° [39°] with respect to ring B [the values for molecule II are given in square parentheses]. The terminal nitro group is rotated by about 16° [10°] to ring C.

Adjacent molecules are linked by C—H . . . π interactions; ring A (in molecule I) is approached by a C(4')—H proton from molecule II [H . . . A 2.45 Å, C(4')—H . . . A 176°], ring B in molecule I is approached by a C(20)-H proton in a neighboring molecule I [H . . . B 2.91 Å, C(20)-H . . . B 145°], and similarly ring B' in molecule II is approached by a C(20')—H proton from another molecule II [H . . . B 2.82 Å, C(20')—H . . . B 153°]. There is also some evidence for a possible weak O . . . π interaction between the nitro group of molecule II and ring C in molecule I with an O(30'). C separation of about 3.22 Å.

Figure 8A:
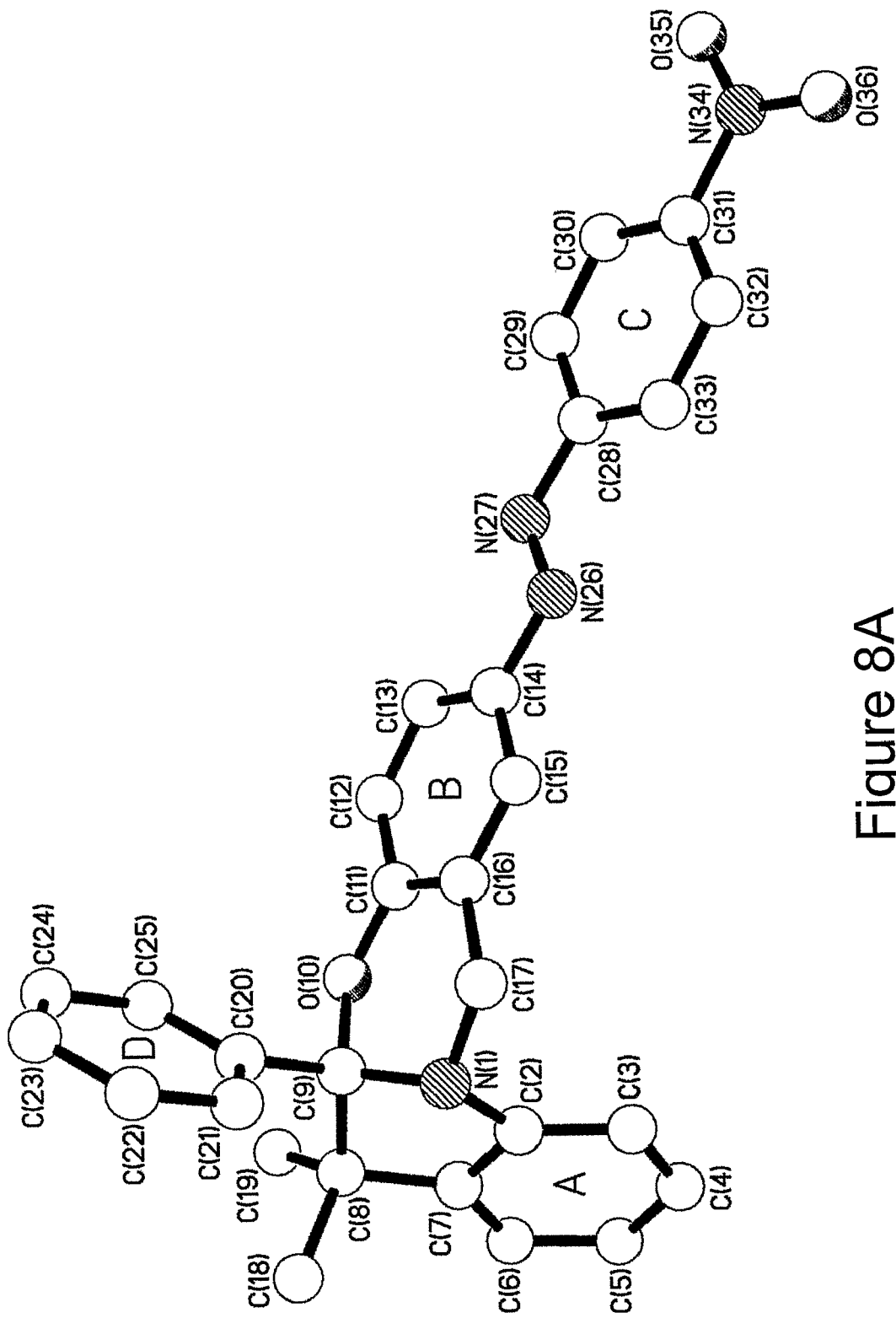
Figure 8B:
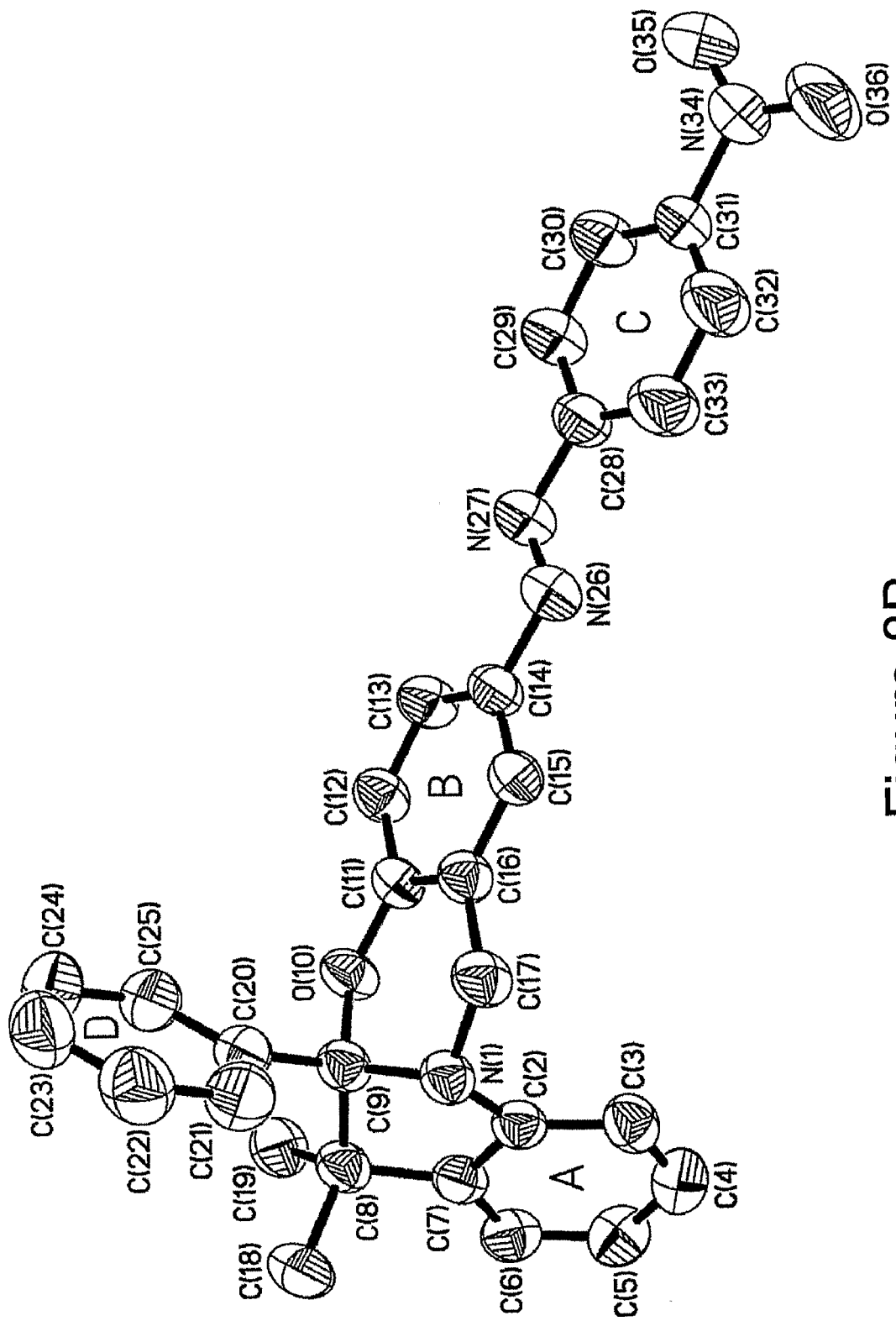
FIG. 8B illustrates it with 50% probability ellipsoids.

The single crystal structure of 8a (the phenyl analog of 7a) is similar, although there is only one independent molecule and the azo-4-nitrophenyl moiety adopts a noticeably different conformation (FIG. 8) where the azo unit is anti with respect to the C(17) carbon center (in both independent molecules of 7a the relationship was gauche). The fused indoline/benzooxazine core of the structure is very similar to that seen in 7a. The indoline ring adopts an envelope-type geometry with C(9) lying about 0.47 Å out of the C$_7$N plane (which is coplanar to within about 0.05 Å), while the benzooxazine ring again has a twisted conformation with N(1) about 0.35 Å "below" and C(9) about 0.28 Å "above" the $C_7O$ plane (which is coplanar to within about 0.03 Å); the $C_7N$ and $C_7O$ planes are inclined by about 80°. The N(1) is again pyramidal, lying about 0.36 Å out of the plane of its substituents, and the nitrogen $2p_z$ orbital is approximately co-linear with the σ orbital of the C(9)-O(10) bond, the O(10)-C(9)-N(1)-lone pair dihedral angle being about 8°. The C—N=N—C unit is again flat (coplanar to better than 0.01 Å), but, unlike in 7a, here it is almost coplanar with both ring B (rotated by about 6°) and ring C (rotated by about 1°). The terminal nitro group is rotated by about 10° to ring C.

Figure 9:
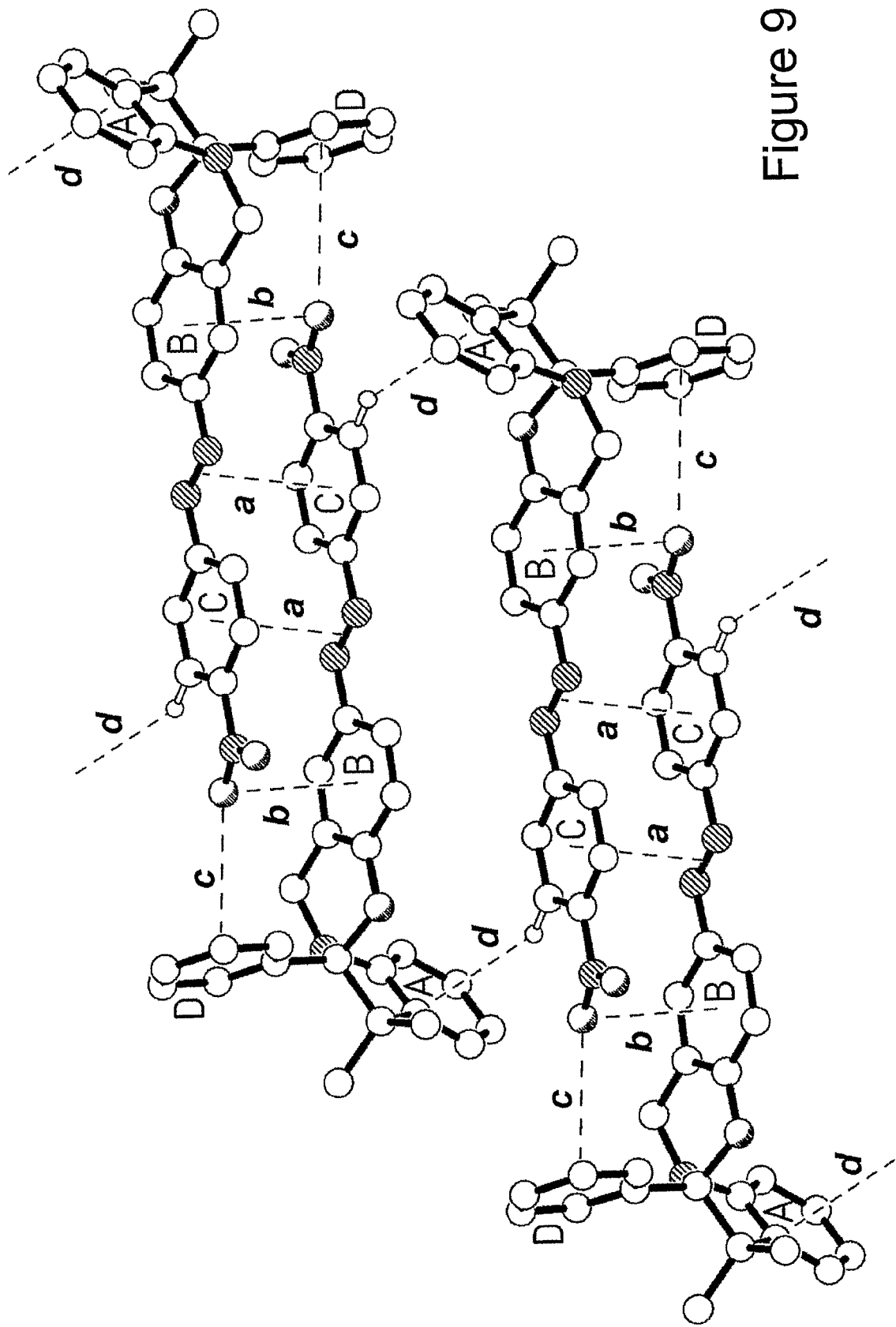
FIG. 9 illustrates the stacking of the 4-nitrophenylazophenolate units of adjacent, centrosymmetrically-related molecules in the crystal of 8a. The phenyl . . . azo interaction (a) has a centroid . . . centroid separation of about 3.40 Å, the O . . . π contacts (b) and (c) have O . . . centroid distances of about 3.13 Å and 3.63 Å, respectively, and the C—H . . . π hydrogen bond has H . . . A 2.88 Å and CH—H . . . A 151°.

The extended structure of 8a is dominated by the stacking of the 4-nitrophenylazophenolate units of adjacent, centrosymmetrically-related molecules linked by a combination of interactions/contacts (FIG. 9). Ring C of one molecule lays above the azo unit of a $C_i$, related counterpart, and vice versa, with a centroid . . . centroid separation of about 3.40 Å (a in FIG. 9). In the same centro-symmetric pair, ring B of one molecule overlays the nitro unit of the other, the closest approach being from O(35) at about 3.13 Å to the ring B centroid (b in FIG. 9). This same oxygen atom also approaches the centroid of ring D in the second molecule, but only at about 3.63 Å (c in FIG. 9). These centro-symmetric pairs of molecules are linked to adjacent pairs across an independent center of symmetry by a couple of C—H . . . π hydrogen bonds from a nitrophenyl hydrogen atom [on C(30)] to the centroid of ring A [H . . . A 2.88 Å, C(30)-H . . . A 151°, d in FIG. 9].

Figure 10:
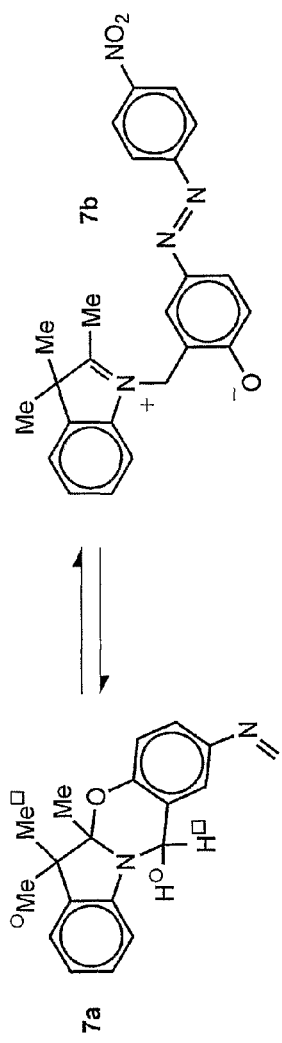
FIG. 10 shows partial $^1$H NMR spectra (500 MHz, acetonitrile-$d_3$, 5 mM) of 7a at 275K (a), 300 K (b), 310 K (c), or 346 K (d).
Figure 10:
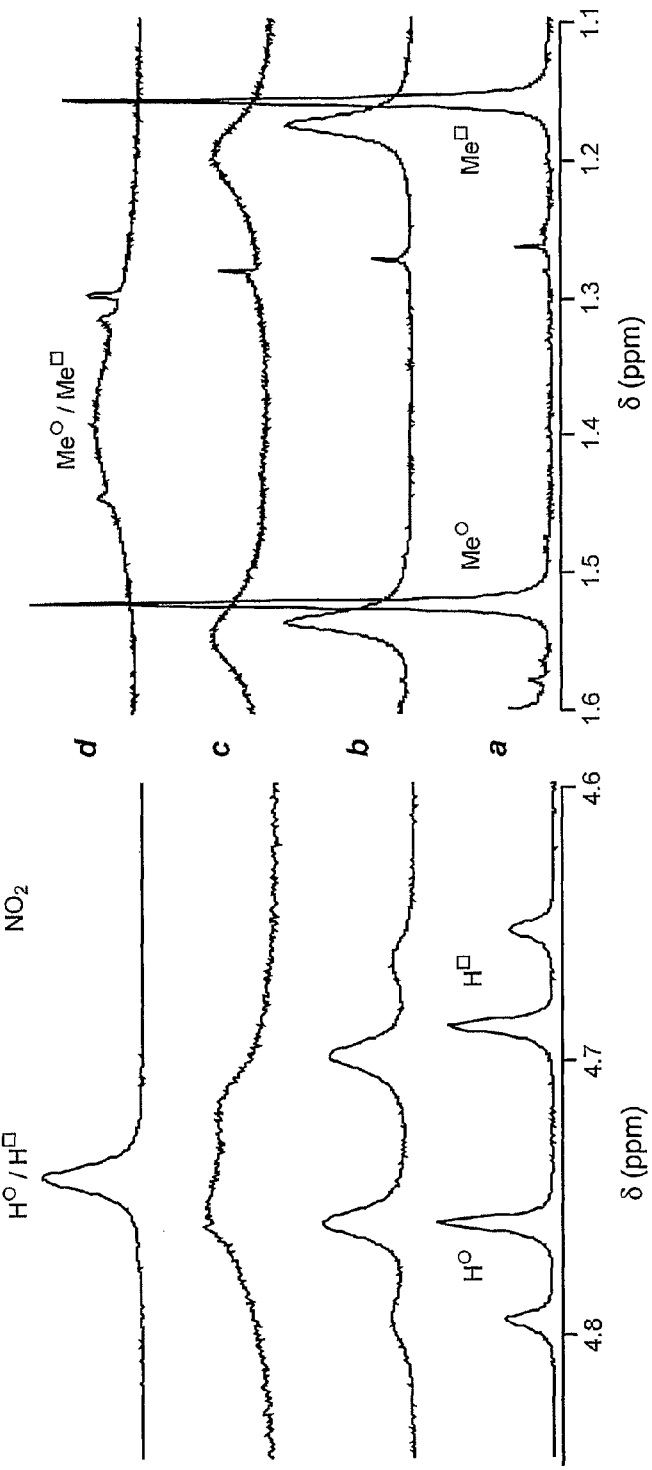
Figure 11:
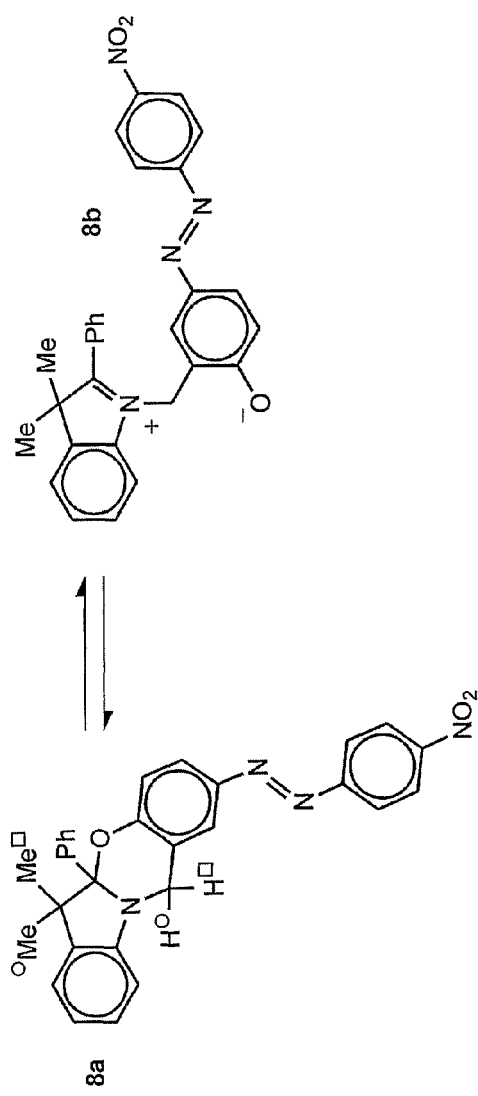
FIG. 11 shows partial $^1$H NMR spectra (500 MHz, acetonitrile-$d_3$, 5 mM) of 8a at 275 K (a), 303 K (b), 310K (c), or 346 K (d).
Figure 11:
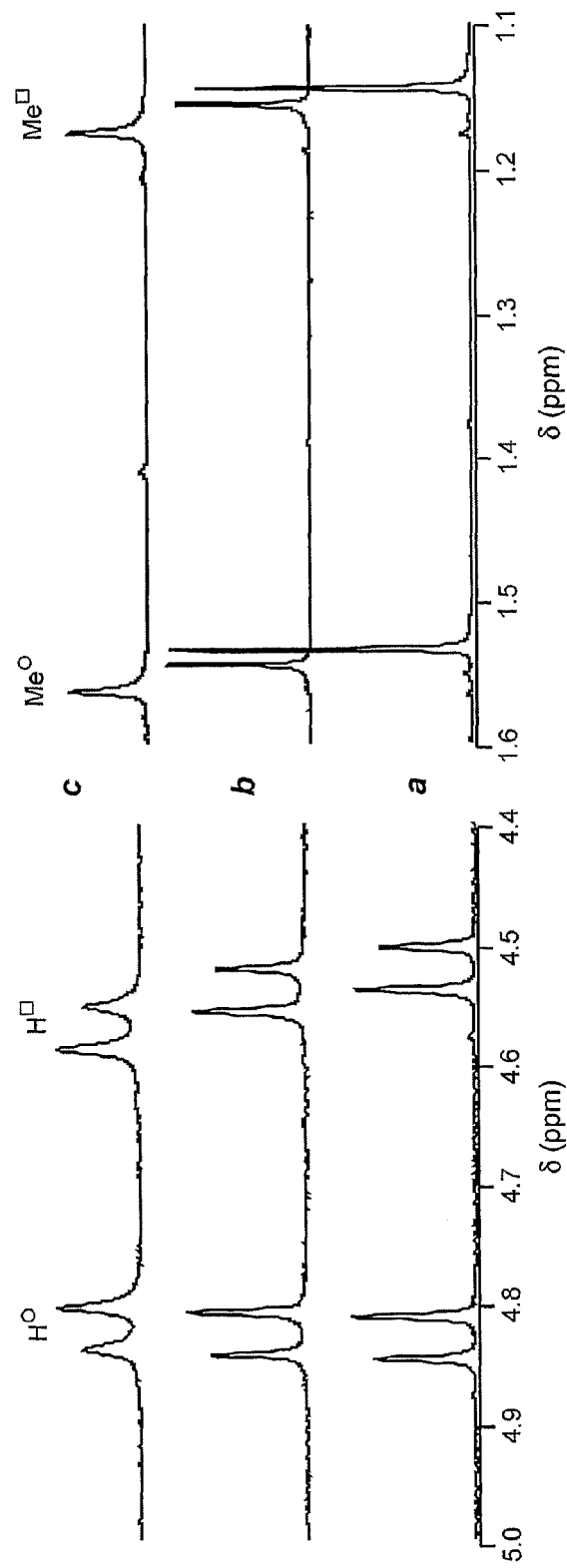

$^1$H NMR Spectroscopy. The chiral center at the junction of the two heterocycles in 7a and 8a imposes two distinct environments on the adjacent pairs of methyl groups (Me° and Me$^\square$ in FIGS. 10-11) and methylene protons (H° and H$^\square$). As a result, the $^1$H NMR spectra of both compounds show two distinct singlets for the protons of Me° and Me$^\square$ and an AB system for H° and H$^\square$, when recorded in acetonitrile-$d_3$ at 275 K (a in FIGS. 10-11). Upon warming the solution, these resonances broaden considerably for both compounds (b and c in FIGS. 10-11) and, eventually, coalesce into single peaks for 7a (d). These changes are a consequence of the interconversion between the two enantiomers of each compound on the $^1$H NMR timescale. This process involves the thermal opening of [1,3]oxazine ring with the formation of 7b and 8b and their re-isomerization to 7a and 8a respectively. The kinetic parameters (Table 1) associated with the ring-opening step can be extracted from the analysis of the temperature dependence of the line widths associated with the singlets for the protons of Me° and Me$^\square$ in the slow-exchange regime. In acetonitrile-$d_3$, the rate constants (k) are about 25 and 0.1 s$^{-1}$ for 7a and 8a, respectively. These values correspond to free energy barriers ($\Delta G^\ddagger$) of about 16 and 19 kcal mol$^{-1}$, respectively. Interestingly, the $\Delta G^\ddagger$ values are dominated by their enthalpic terms ($\Delta H^\ddagger$), while the entropic contributions are negligible ($\Delta S^\ddagger$). In toluene-$d_8$, the ring-opening process is significantly slower. The k value for 7a decreases by four orders of magnitude with a concomitant increase of about 4.5 kcal mol$^{-1}$ in $\Delta G^\ddagger$. In the case of 8a, the process is so slow that the $^1$H NMR spectrum remains virtually unchanged over a broad range of temperatures.

Figure 12:
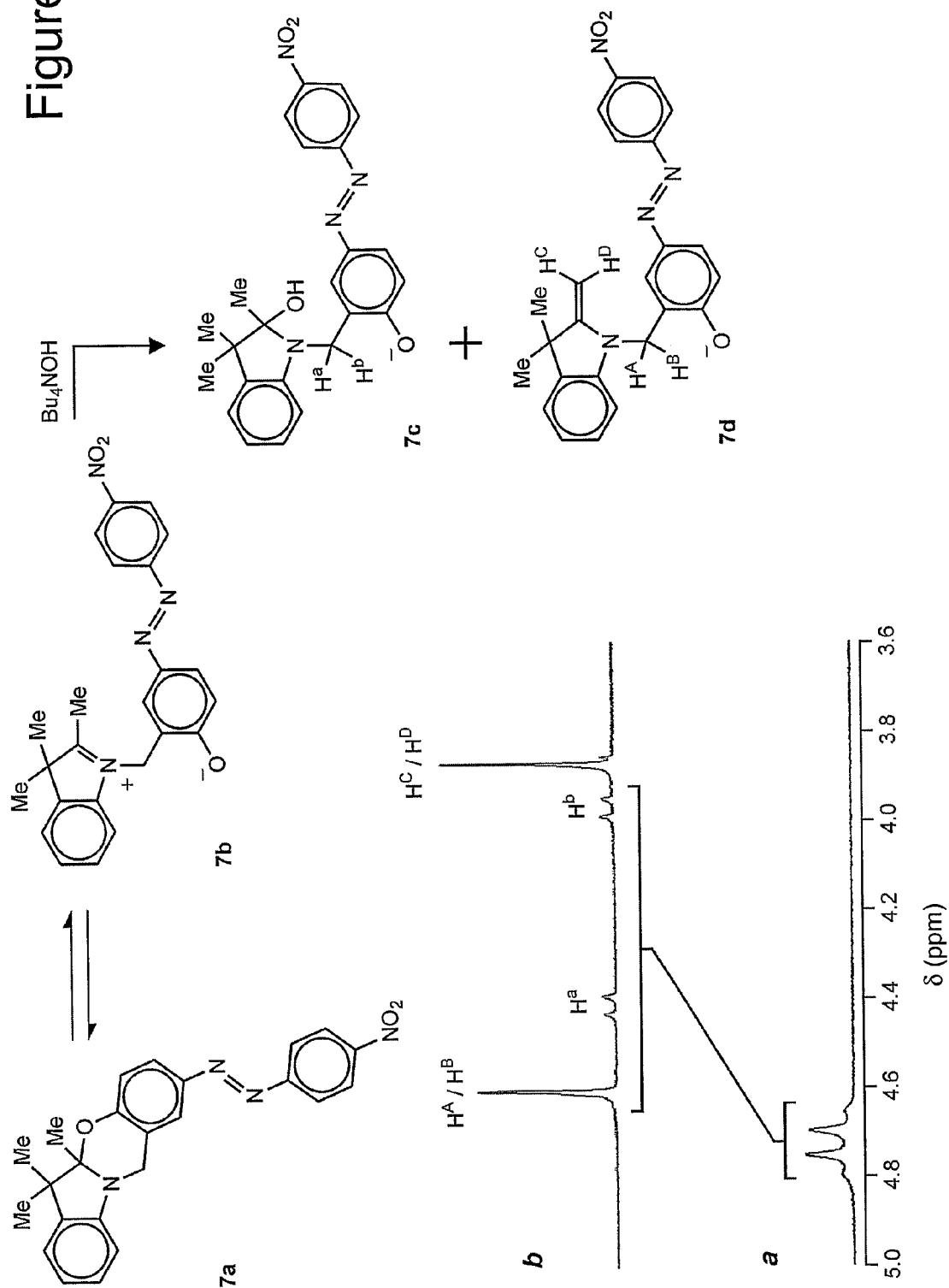
FIG. 12 shows partial $^1$H NMR spectra (400 MHz, acetonitrile-$d_3$, 10 mM) of 7a before (a) or after (b) the addition of $Bu_4NOH$ (6 eq.).
Figure 13:
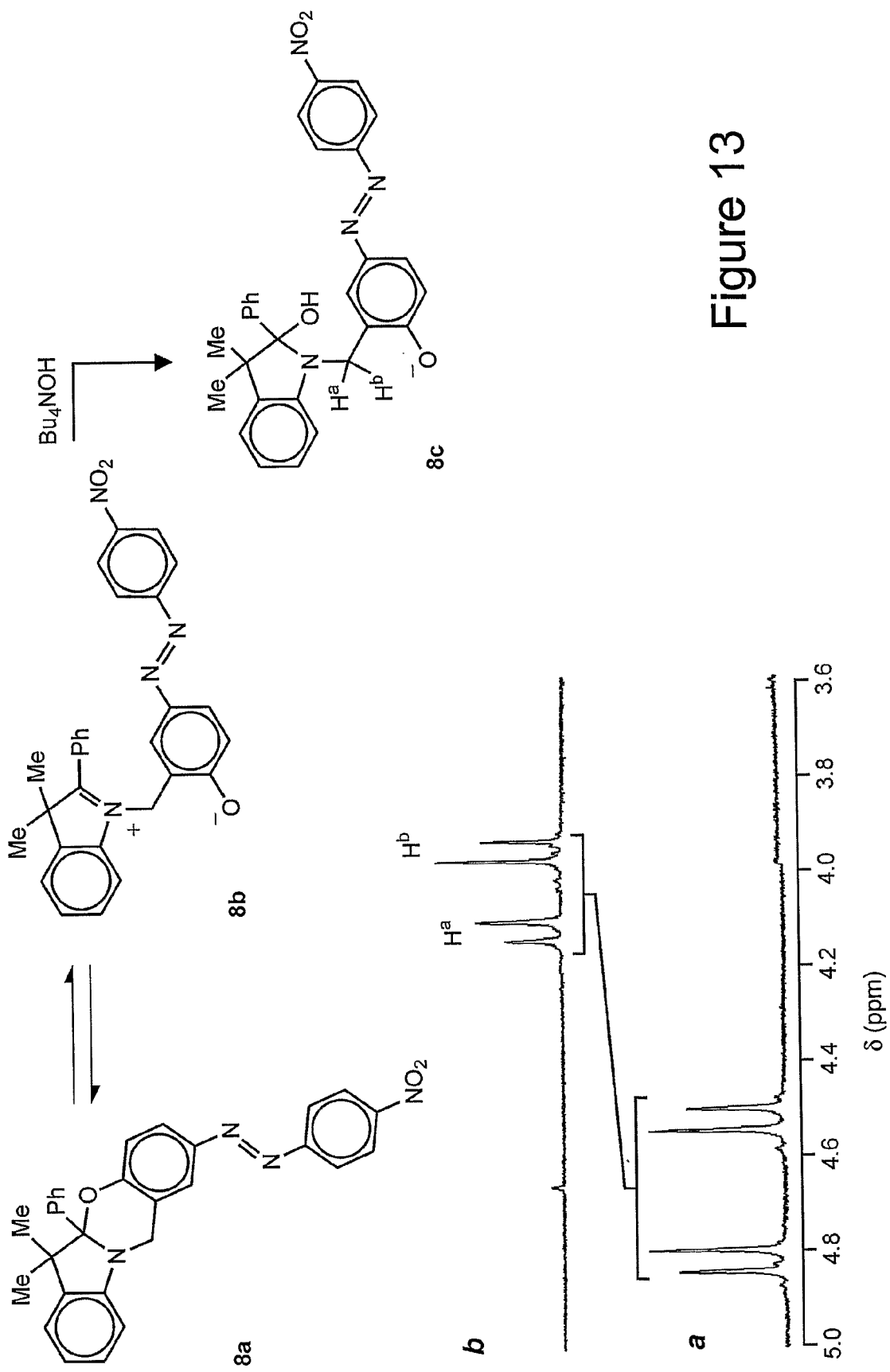
FIG. 13 shows partial $^1$H-NMR spectra (400 MHz, acetonitrile-$d_3$, 10 mM) of 8a before (a) or after (b) the addition of $Bu_4NOH$ (4 eq.).

The quantitative transformation of 1a into 1c (FIG. 1) causes drastic changes in the $^1$H NMR spectrum.[38] The two oxazines 7a and 8a show essentially the same behavior. Their treatment with Bu$_4$NOH results in the formation of the corresponding hemiaminals 7c and 8c (FIGS. 12-13). In both instances, the chemical shift of the diastereotopic methylene protons decreases, but their

TABLE 1

Kinetic parameters associated with the ring opening of 7a and 8a at 298 K.[a]

| Solvent | Compound | k (s$^{-1}$) | $\Delta G^\ddagger$ (kcal mol$^{-1}$) | $\Delta H^\ddagger$ (kcal mol$^{-1}$) | $-\Delta S^\ddagger$ (kcal mol$^{-1}$ K$^{-1}$) |
|---|---|---|---|---|---|
| Acetonitrile-$d_3$ | 7a | 25 ± 2 | 15.54 ± 0.04 | 15.0 ± 0.2 | 0.002 ± 0.001 |
| | 8a | 0.10 ± 0.02 | 18.82 ± 0.11 | 18.5 ± 0.9 | 0.001 ± 0.003 |
| Toluene-$d_8^b$ | 7a | 0.011 ± 0.004 | 20.17 ± 0.23 | 21.4 ± 1.3 | −0.004 ± 0.004 |

[a]The rate constant (k), free energy ($\Delta G^\ddagger$), enthalpy ($\Delta H^\ddagger$) and entropy ($\Delta S^\ddagger$) of activation were determined by variable-temperature $^1$H NMR spectroscopy. Below the coalescence temperature, two well-separated singlets can be observed for the protons of Me° and Me° in the $^1$H NMR spectra (a-c in FIGS. 9 and 10). Under these conditions, the line width ($\Delta v$) of either one of the two singlets is related to the rate constant (k) of the degenerate site-exchange process according to equation (1), where $\Delta v_0$ is the line width at the stopped-exchange limit (Nelson, Nuclear Magnetic Resonance Spectroscopy, Prentice Hall: Upper Saddle River, 2003). Following this protocol, k can be determined at any temperature (T) within the slow-exchange regime. A plot of ln (k T$^{-1}$) against T$^{-1}$ can then be fitted to equation (2), where R is the gas constant, to extract the enthalpy ($\Delta H^\ddagger$) and entropy ($\Delta S^\ddagger$) of activation. Finally, the free energy ($\Delta G^\ddagger$) of activation can be calculated at any T using equation (3).

$$k = \pi(\Delta v - \Delta v_0) \quad (1)$$

$$\ln \frac{k}{T} = -\frac{\Delta H^\ddagger}{RT} + \frac{\Delta S^\ddagger}{R} + 23.7 \quad (2)$$

$$\Delta G^\ddagger = \Delta H^\ddagger - T\Delta S^\ddagger \quad (3)$$

[b]In toluene-$d_8$, the line widths of the singlets associated with the pair of methyl protons of 8a remain approximately constant in the examined temperature range (275 K to 363 K). As a result, the kinetic parameters for the ring opening of this compound could not be determined.

AB system is maintained, confirming the presence of a chiral center in 7c and 8c. A second product is also formed in the case of 7. Indeed, the methyl group on its chiral center is relatively acidic and is partially deprotonated upon treatment with Bu$_4$NOH to form 7d (FIG. 12). The ratio between 7c and 7d can be estimated to be 70:30 from the integrals of the resonances associated with the methylene protons. The formation of the two hemiaminals 7c and 8c is further confirmed by the appearance of peaks at m/z 431 and 493 in the corresponding fast atom bombardment mass spectra.

Figure 14:
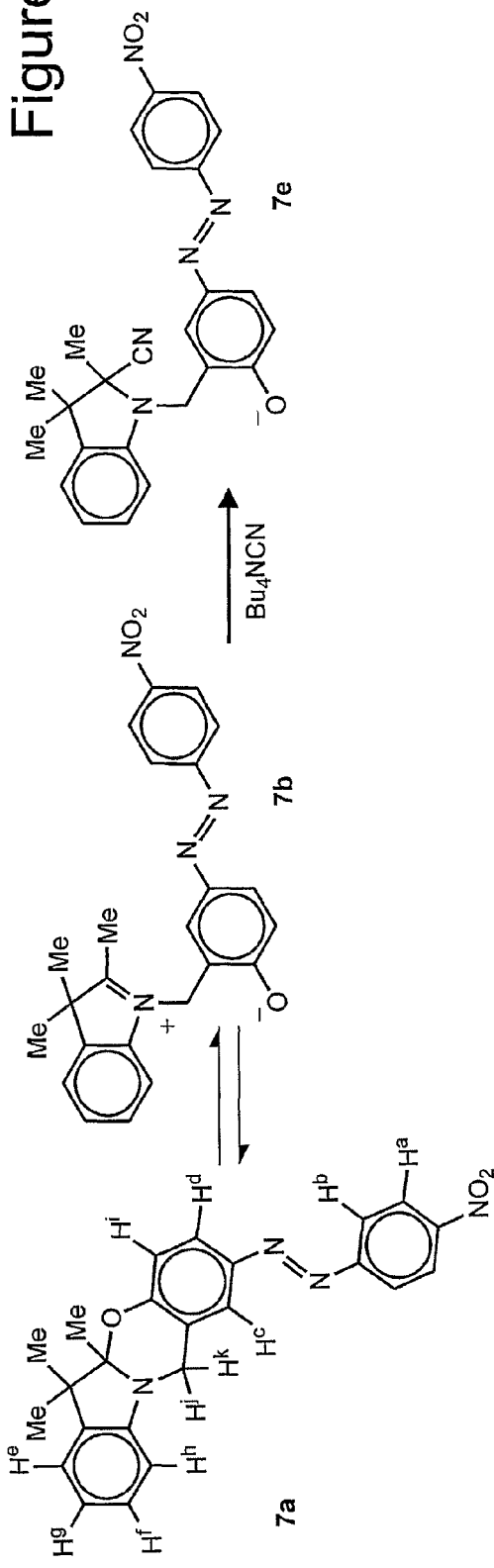
FIG. 14 shows partial $^1$H NMR spectra (400 MHz, acetonitrile-$d_3$, 10 mM) of 7a before (a) or after (b) the addition of $Bu_4NCN$ (10 eq.).
Figure 14:
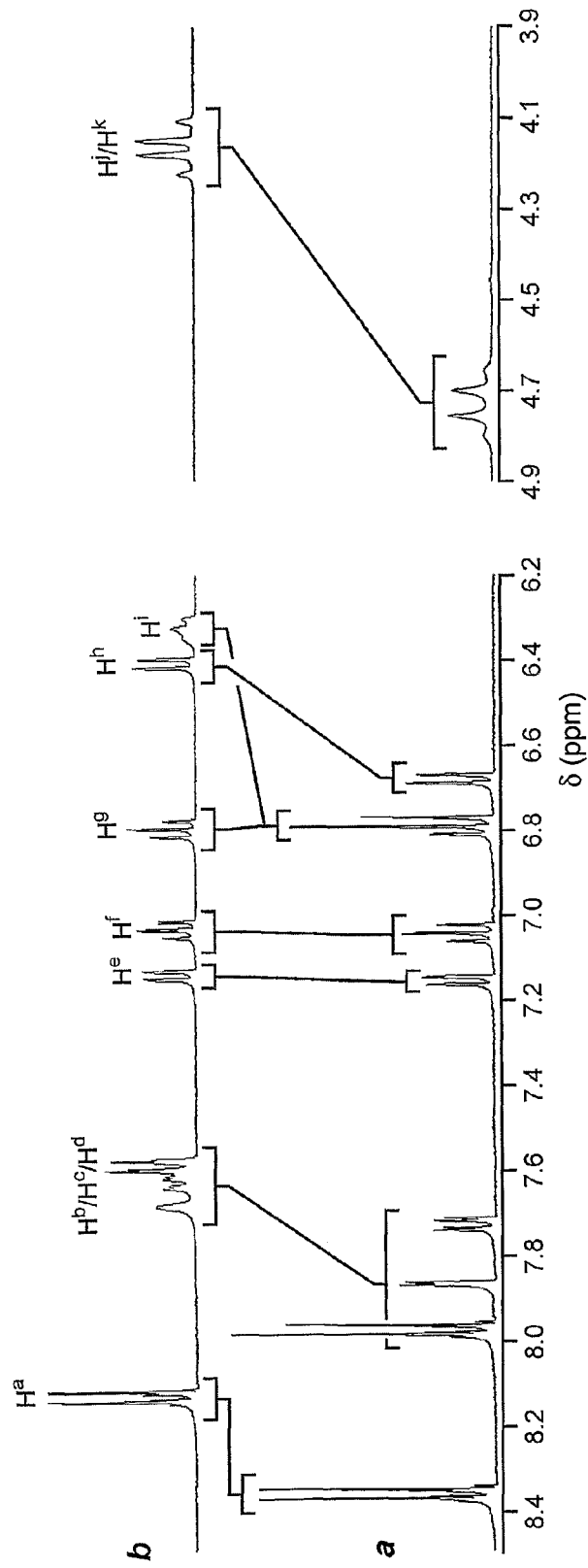
Figure 15:
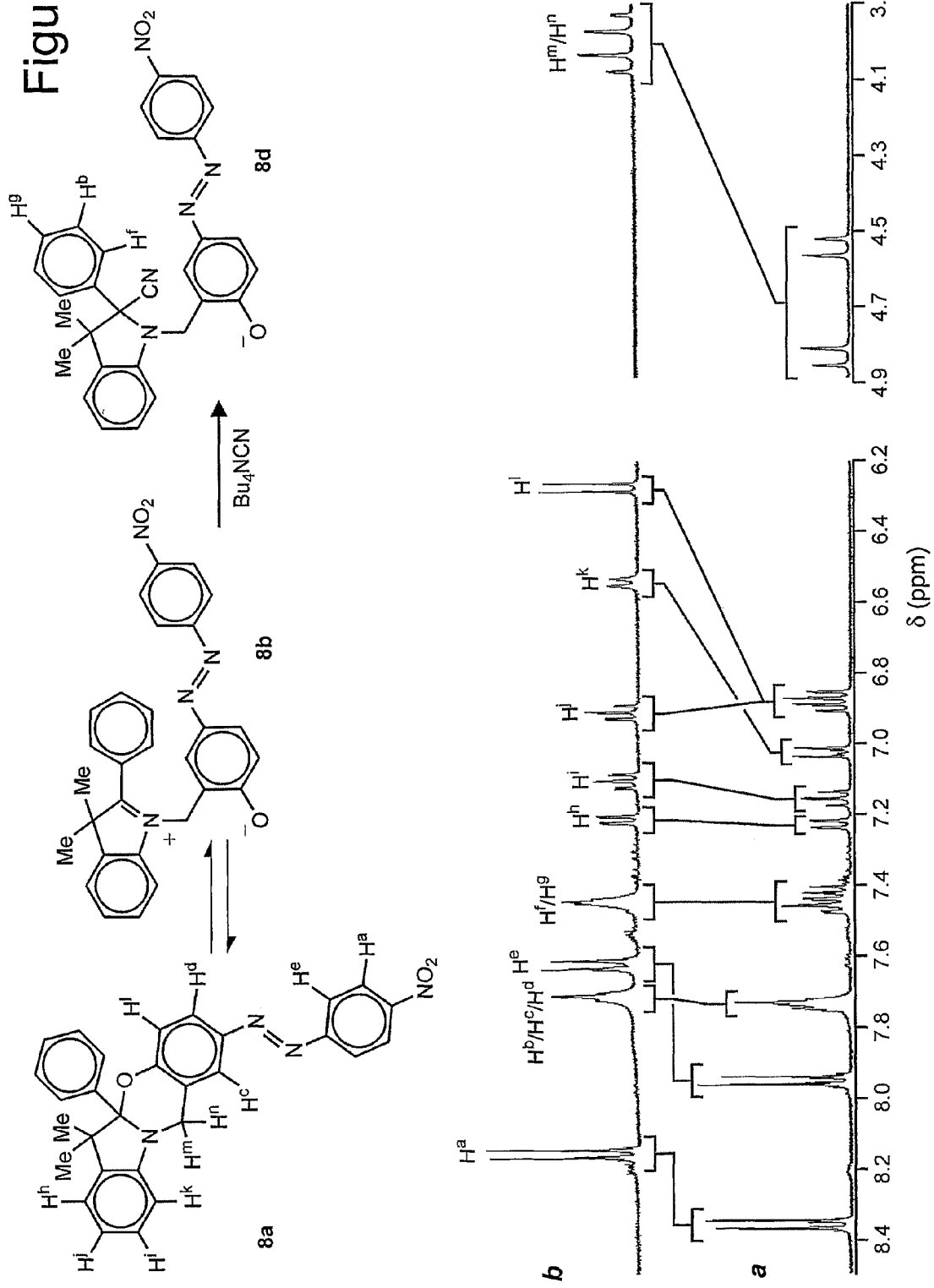
FIG. 15 shows partial $^1$H-NMR spectra (400 MHz, acetonitrile-$d_3$, 10 mM) of 8a before (a) or after (b) the addition of $Bu_4NCN$ (20 eq.).

The changes imposed on the $^1$H NMR spectra of 7a and 8a by the addition of Bu$_4$NOH can be replicated with Bu$_4$NCN. In both instances, the cyanide anion attacks the indolium cations of 7b and 8b to form quantitatively 7e and 8c, respectively (FIGS. 14-15). From these transformations, the chemical shifts of most aromatic protons decrease (a and b in FIGS. 14-15). For both oxazine compounds, the largest change (–0.45 ppm for 7a and –0.61 ppm for 8a) is observed for the proton in the ortho position relative to the phenolate oxygen atom (H$^f$ for 7a and H$^f$ for 8a). Once again, the AB system for the methylene protons is maintained with the transformation of 7a into 7e and of 8a into 8c, but moves by –0.57 ppm for 7 and –0.69 ppm for 8. Furthermore, the fast atom bombardment mass spectra show the appearance of peaks at m/z 441 and 503 in support of the formation of 7e and 8c, respectively.

Figures 16A, 16B:
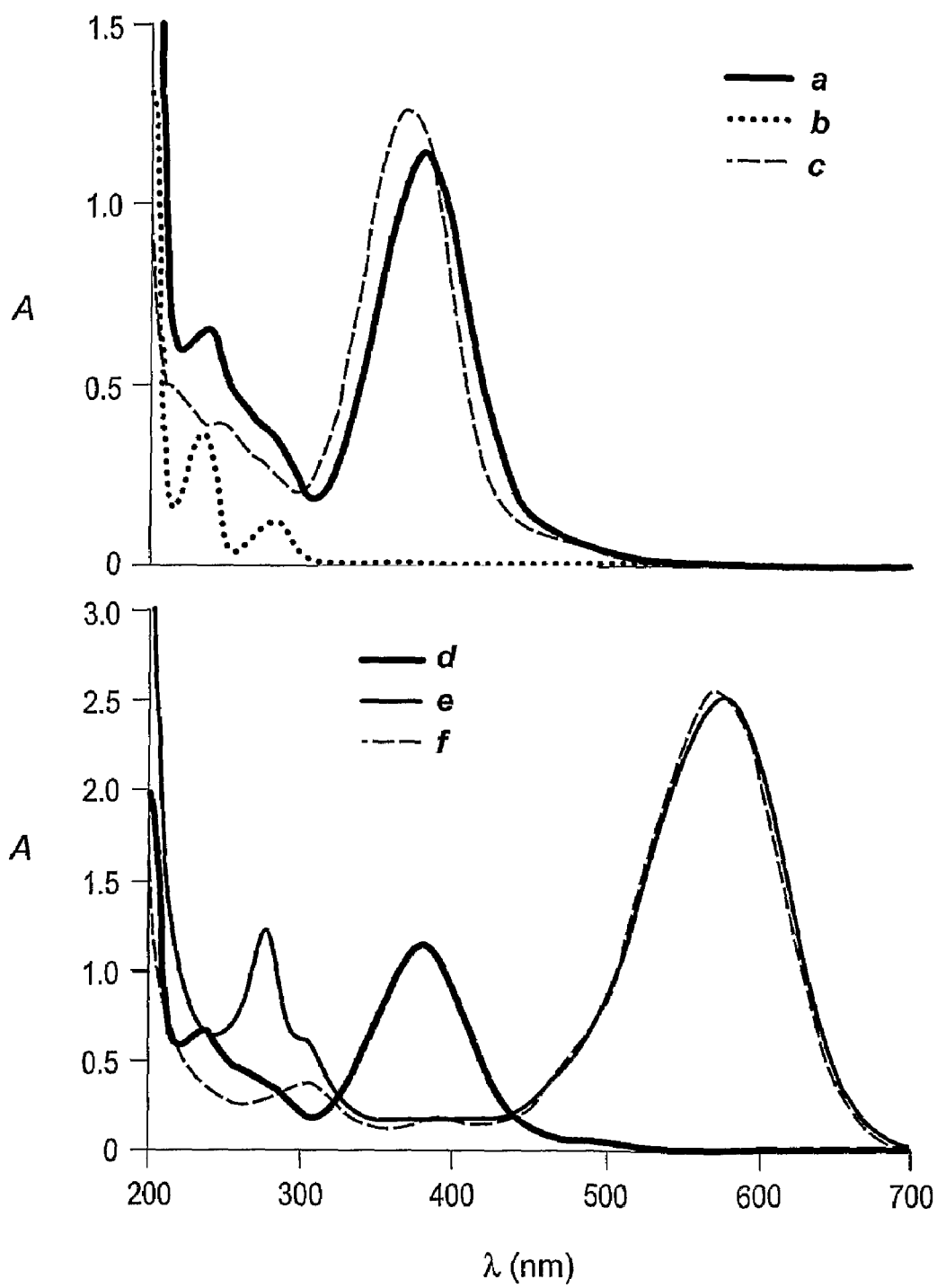
FIGS. 16A and 16B show steady-state absorption spectra (0.1 mM, MeCN, 298 K) of 7a (a), 9 (b), 11 (c), 7a before (d) or after (e) the addition of $Bu_4NOH$ (1 eq.), or 12 (f).

Steady-State Absorption Spectroscopy. The steady-state absorption spectra of the two [1,3]oxazines 7a and 8a (a in FIGS. 16-17) resemble the sum of those of the model compounds 9 or 10 (b) and 11 (c). In particular, an intense band for the $\pi \rightarrow \pi^*$ transition of the 4-nitrophenylazophenyl chromophore is evident at 380 nm for 7a and at 371 nm for 8a (Table 2). Upon addition of Bu$_4$NOH, this absorption disappears with the concomitant appearance of a band at about 575 nm (d and e in FIGS. 16-17) for the 4-nitrophenylazophenolate chromophores of 7c/7d and 8c. Indeed, the spectrum of the model 4-nitrophenylazophenolate 12 (f in FIGS. 16-17) shows an absorption at 576 nm with a molar extinction coefficient close to 50 mM$^{-1}$ cm$^{-1}$ (Table 2).

TABLE 2

Absorption wavelengths (λ) and molar extinction coefficients (ε) of the oxazines 7a and 8a and of the model compounds 9-12 in MeCN at 298 K.$^a$

| Compound | λ (nm) | ε (mM$^{-1}$ cm$^{-1}$) |
| --- | --- | --- |
| 7a | 380 | 23.0 ± 1.2 |
| 8a | 371 | 22.0 ± 1.1 |
| 9 | 283 | 2.2 ± 0.1 |
| 10 | 281 | 3.9 ± 0.2 |
| 11 | 371 | 26.1 ± 1.3 |
| 12 | 576 | 50.4 ± 1.1 |

$^a$The model compounds are shown in the following diagram. The λ and ε of the phenolate 12 were determined by recording the absorption spectrum of the corresponding phenol in the presence of Bu$_4$NOH (4 eq.).

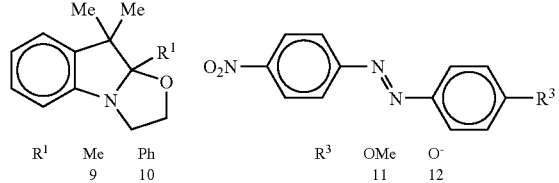

Figure 18A:
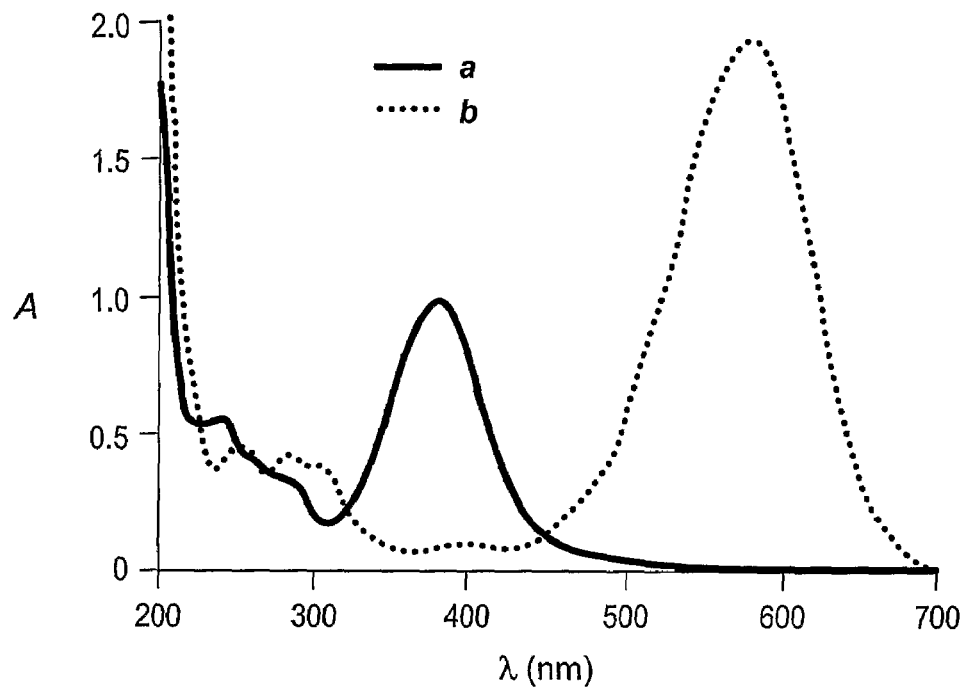
FIG. 18A shows steady-state absorption spectra (0.1 mM, MeCN, 298 K) of 7a before (a) or after (b) the addition of $Bu_4NCN$ (15 eq.).
Figure 18B:
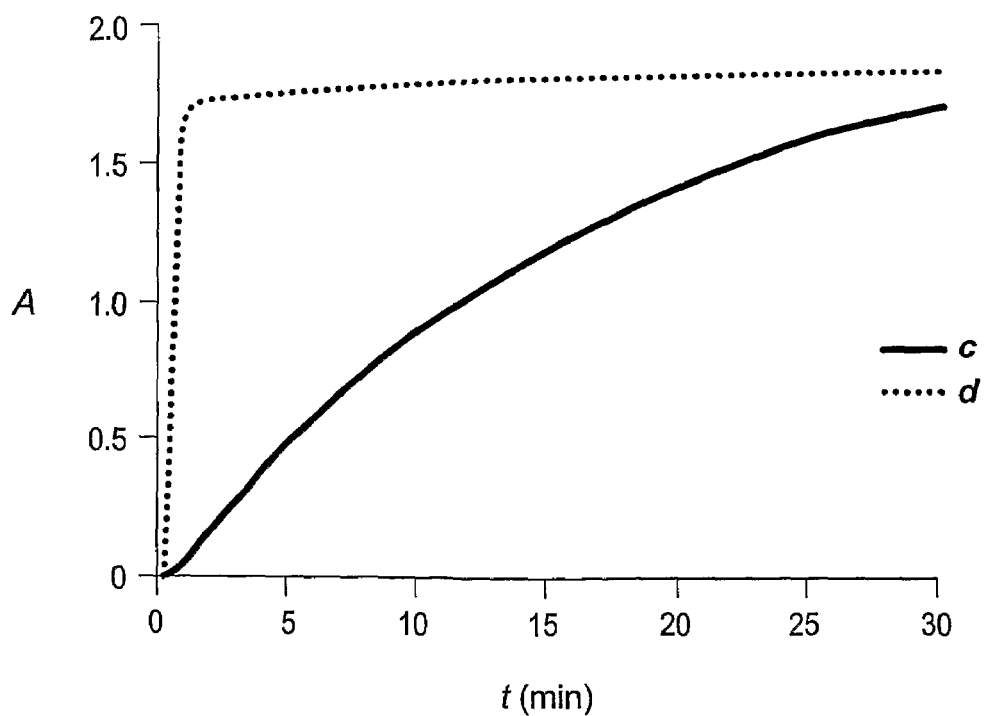
FIG. 18B shows a kinetic trace of the evolution of absorbance at 581 nm for a solution (0.1 mM, MeCN, 298 K) of 7a (c) or 8a (d) after the addition of $Bu_4NCN$ (1.5 eq. for 7a and 15 eq. for 8a).

The addition of Bu$_4$NCN to acetonitrile solutions of 7a and 8a causes similar absorption changes (a and b in FIGS. 18-19). Once again, the characteristic absorption of a 4-nitrophenylazophenolate chromophore can be observed at about 580 nm only in the presence of the nucleophile. The chromogenic transformation of 7a, however, is significantly faster than that of 8a. The 4-nitrophenylazophenolate absorbance of the product reaches a stationary value in less than one minute after the addition of only 1.5 eq. of Bu$_4$NCN to 7a (c in FIG. 18). Instead, more than 30 min are required to complete the transformation of 8a even in the presence of up to 15 eq. of Bu$_4$NCN (d in FIG. 18). These observations are in full agreement with the kinetic parameters (Table 1) determined for the ring opening of 7a and 8a by $^1$H NMR spectroscopy. Indeed, these data show that the ring opening of 8a is two orders of magnitude slower than that of 7a.

The relatively fast calorimetric response of 7a to cyanide can be used to sense this particular anion in aqueous environments. In fact, the addition of NaCN in sodium phosphate buffer (pH 7.6) to an acetonitrile solution of 7a results in the appearance of the 4-nitrophenylazophenolate absorption band (a in FIG. 20). This band cannot be observed if the acetonitrile solution of 7a is treated with sodium phosphate buffer lacking NaCN (b in FIG. 20). Similarly, halide salts have essentially no influence on 7a under otherwise identical conditions. Indeed, the absorption spectra of acetonitrile solutions of 7a do not show any increase in absorbance in the visible region even after the addition of sodium phosphate buffer containing large amounts (10 mM) of NaF (c in FIG. 20), NaCl (d), NaBr (e), or NaI (f).

Figure 21:
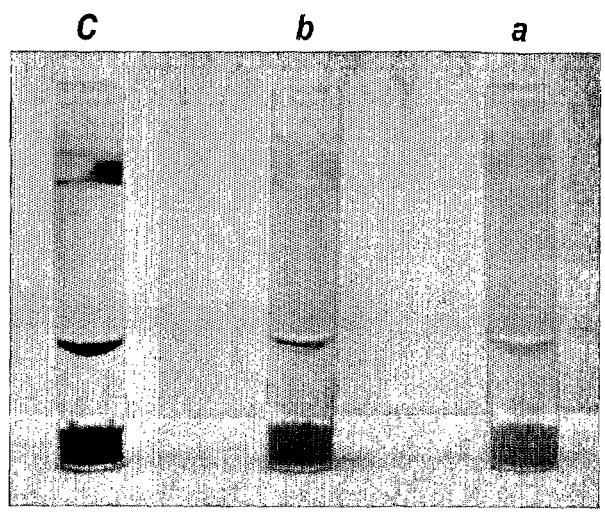
FIG. 21 shows solutions of 7a (1 mM, 200 μL, dichloroethane, 298 K) 4 and $Bu_4NCl$ (1 M) and overlaid sodium phosphate buffer (500 μL, pH 9.0) without (a) or with 10 (b) or 100 μM (c) of NaCN.
Figure 22A:
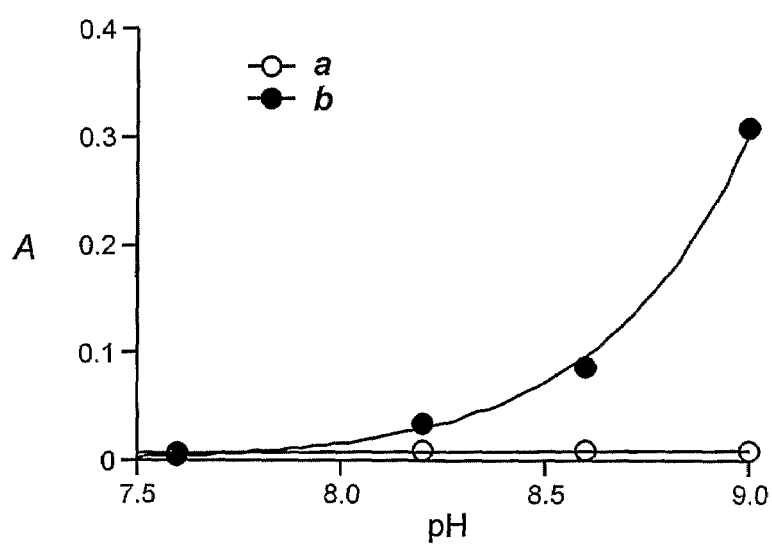
FIG. 22A shows absorbance at 581 nm of a solution of 7a (1 mM, 200 μL, dichloroethane, 298 K) and $Bu_4NCl$ (1 M) after treatment with sodium phosphate buffer (300 μL) without (a) or with (b) NaCN (0.1 mM) and dilution with dichloroethane (470 μL).
Figure 22B:
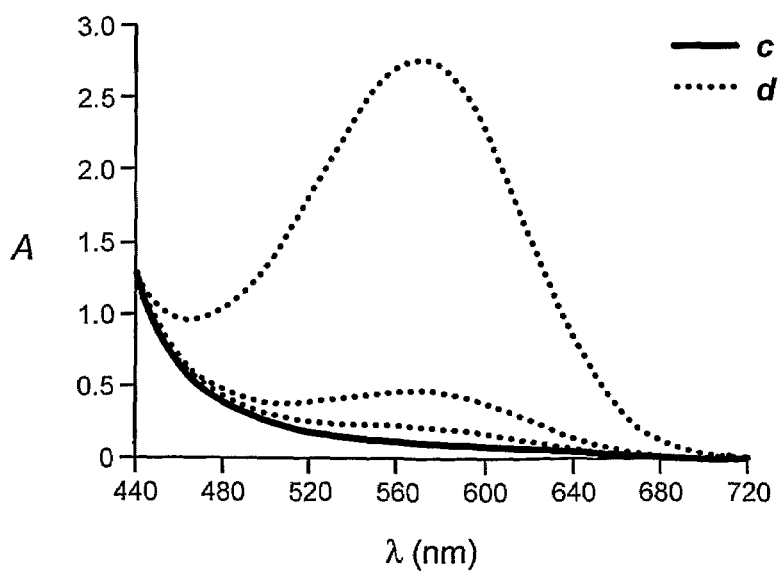
FIG. 22B shows steady-state absorption spectra of solutions of 7a (1 mM, 200 μL, dichloroethane, 298 K) and $Bu_4NCl$ (1 M) after treatment with sodium phosphate buffer (100 μL, pH 9.0) without (c) or with (d) increasing amounts of NaCN (1 μM to 100 μM) and dilution with dichloroethane (120 μL).

Acetonitrile solutions of 7a respond to aqueous solutions of cyanide with a detectable absorbance change only if the cyanide concentration is greater than 0.1 mM. The chromogenic response, however, improves considerably when 7a is dissolved in dichloroethane together with Bu$_4$NCl. The resulting organic solutions change color when treated with aqueous solutions containing micromolar concentrations of cyanide (a-c in FIG. 21). Presumably, the tetrabutyl ammonium salt facilitates the transfer of cyanide anions from the aqueous to the organic phase and encourages the chromogenic transformation. Furthermore, the chromogenic transformation is particularly sensitive to the pH of the aqueous phase and has an optimal response to cyanide at a pH of about 9.0. Indeed, the absorbance of the organic solution at 581 nm remains negligible up this particular pH value (a in FIG. 22A) in the absence of cyanide salts in the aqueous phase. Instead, the absorbance increases significantly with the pH of the aqueous solution when this particular phase contains cyanide anions (b in FIG. 22A). At a pH of 9.0, even micromolar concentrations of cyanide in the aqueous phase are sufficient to impose a detectable change on the absorbance of the organic phase (c and d in FIG. 22B).

Figure 23A:
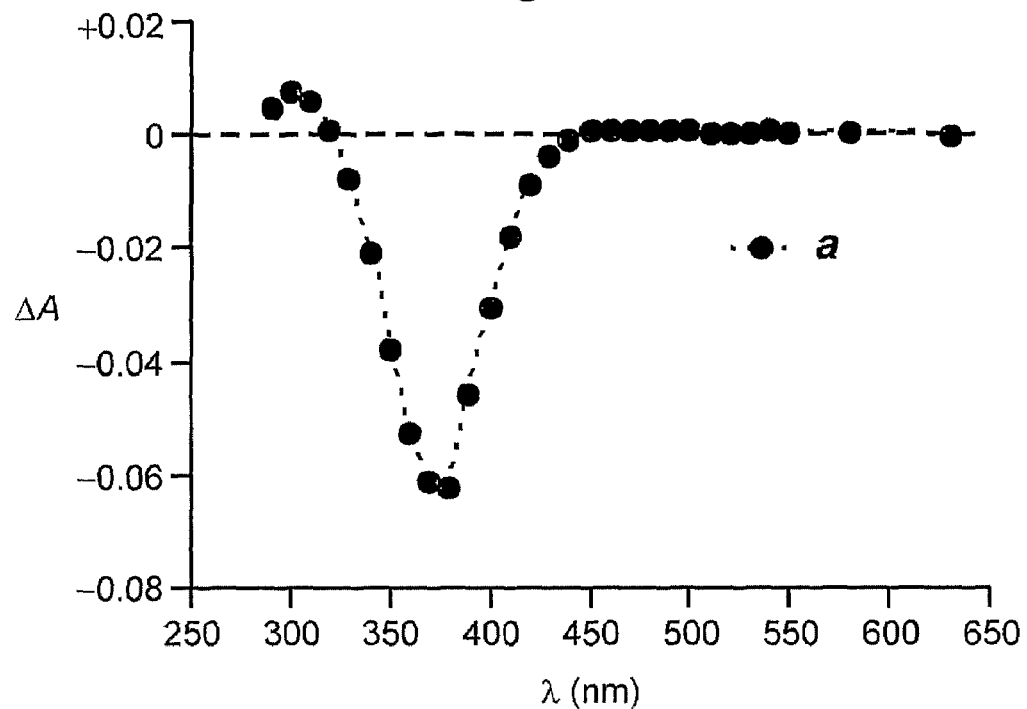
FIG. 23A shows a transient absorption spectrum (a) of 8a recorded 4 μs after the laser pulse (355 nm, 6 ns, 8 mJ, 0.1 mM, MeCN, 295 K).
Figure 23B:
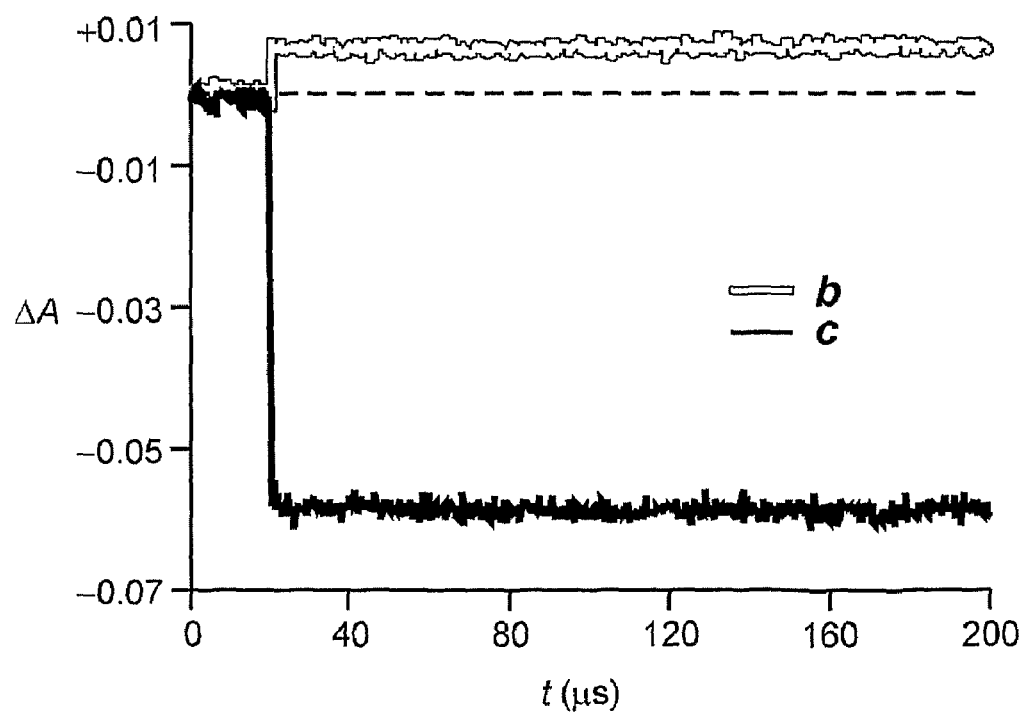
FIG. 23B shows a kinetic trace of the evolution of absorbance at 290 nm (b) or 380 nm (c) upon laser excitation.
Figure 24:
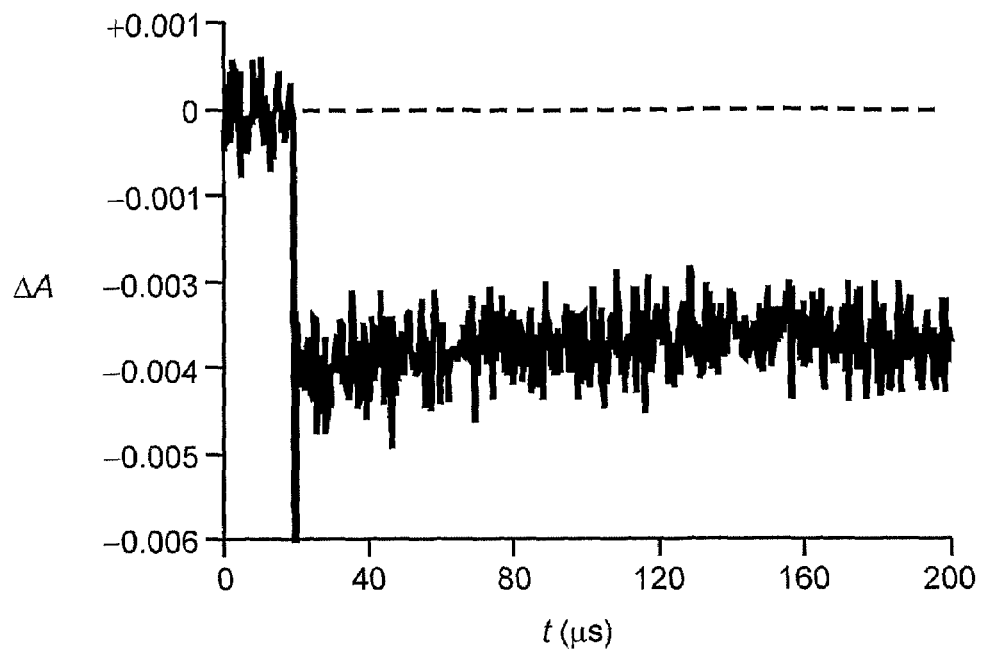
FIG. 24 shows a kinetic trace of the evolution of absorbance at 380 nm upon laser excitation (355 nm, 6 ns, 8 mJ, 295 K) of a polymethylmethacrylate film of 8a (5%).

Transient Absorption Spectroscopy. The laser excitation of the [1,3]oxazine 1a induces the formation of the ring-opened isomer 1b in less than 6 ns with a quantum yield of 0.1 in aerated acetonitrile.[38] The photogenerated species reverts to the original form with a lifetime of 22 ns. In principle, a similar process can also occur upon excitation of the [1,3] oxazines 7a and 8a. In order to explore this possibility, we analyzed 8a by laser flash photolysis. In contrast to the behavior of 1a, the characteristic absorption of 8b cannot be detected in the resulting transient absorption spectra. Instead, an increase in absorbance at 290 nm and bleaching of the $\pi \rightarrow \pi^*$ transition of the 4-nitrophenylazophenyl chromophore at 380 nm are evident in the spectrum recorded after 4 μs from the laser pulse (a in FIG. 23A). Both transient bands remain constant in the microsecond domain (b and c in FIG. 23B), but eventually disappear with millisecond-second timescales. The transient absorption spectra of 8a trapped in polymethylmethacrylate matrices show essentially the same temporal evolution (FIG. 24). In fact, the steady-state absorption spectra recorded before and after the laser flash photolysis experiment are virtually indistinguishable. These observations are consistent with the photoinduced trans→cis isomerization of the 4-nitrophenylazophenyl chromophore of 8a, followed by the thermal cis→trans re-isomerization, and exclude the photoinduced ring opening observed for 1a.

Cyanide anion can be detected colorimetrically relying on the opening of a [1,3]oxazine ring and the concomitant formation of a phenolate chromophore. Chromogenic compounds can be prepared by fusing a benzooxazine ring to an indoline fragment. The [1,3]oxazine ring of the resulting compounds opens and closes rapidly on the $^1$H NMR time scale in acetonitrile-d$_3$ at ambient temperature. The free energy barrier for the ring-opening process increases when either (1) the substituent on the carbon atom at the junction of the two heterocycles changes from a methyl to a phenyl group or (2) the solvent varies from acetonitrile-d$_3$ to toluene-d$_8$. The ring-opened isomer is short lived, but can be trapped with the addition of a nucleophile. For example, a cyanide anion can attack the electrophilic indolium cation of this species preventing the ring-closing process. The result is the quantitative formation of a cyanoamine and the appearance of an intense band in the visible region of the absorption spectrum, corresponding to a phenolate chromophore. The chromogenic response of the phenyl-substituted oxazine to cyanide requires several minutes to reach a steady state. Instead, the coloration of the methyl-substituted oxazine occurs on a timescale of seconds. Furthermore, these compounds are not affected by fluoride, chloride, bromide, or iodide anions, which are common interferents in conventional assays for cyanide.[32-37] Finally, dichloroethane solutions of this oxazine and a phase-transfer catalyst respond to aqueous solutions containing micromolar amounts of cyanide with a noticeable absorbance increase in the visible region, offering detection limits comparable to those of the best chemosensors available for this anion.[36-37] Thus, our operating principles for the colorimetric detection of cyanide can eventually evolve into fast and simple assays for the determination of relatively small amounts of this toxic analyte in water without suffering from the deleterious interference of commonly present anions.

General Methods. Chemicals were purchased from commercial sources and used as received with the exception of CH$_2$Cl$_2$, which was distilled over CaH$_2$. Compounds 9 and 10 were prepared according to literature protocols (Raymo et al., *J. Org. Chem.* 68, 4158-4169, 2003; Tomasulo et al., *Org. Lett.* 7, 1109-1112, 2005). All reactions were monitored by thin-layer chromatography, using aluminum sheets coated with silica (60, F$_{254}$). High-performance liquid chromatography (HPLC) was performed with a Varian ProStar system coupled to a ProStar 330 photodiode array detector. Analytical (column dimensions=4.6 mm×250 mM, flow rate=1.0 mL min$^{-1}$, injection volume=10 μL, sample concentration=0.1 mM) and semi-preparative (column dimensions=21.4 mm×250 mm, flow rate=10 mL min$^{-1}$, injection volume=10 mL, sample concentration=0.1 mM) Varian Microsorb BDS columns were employed. Retention time (RT) and peak asymmetry (PA) were determined at a wavelength of 254 nm. Average purity parameter (APP) was calculated for the peak heart in the range of wavelengths from 215 nm to 700 nm. Melting points (mp) were determined with an Electrothermal MeI-Temp apparatus. Fast atom bombardment mass spectra (FABMS) were recorded with a VG Mass Lab Trio-2 spectrometer using a 3-nitrobenzyl alcohol matrix. Nuclear magnetic resonance (NMR) spectra were recorded with a 300 MHz, 400 MHz, or 500 MHz Bruker Avance spectrometer. Absorption spectra were recorded with a Varian Cary 100 Bio spectrometer using quartz cells with a path length of 0.5 cm.

Figure 25:
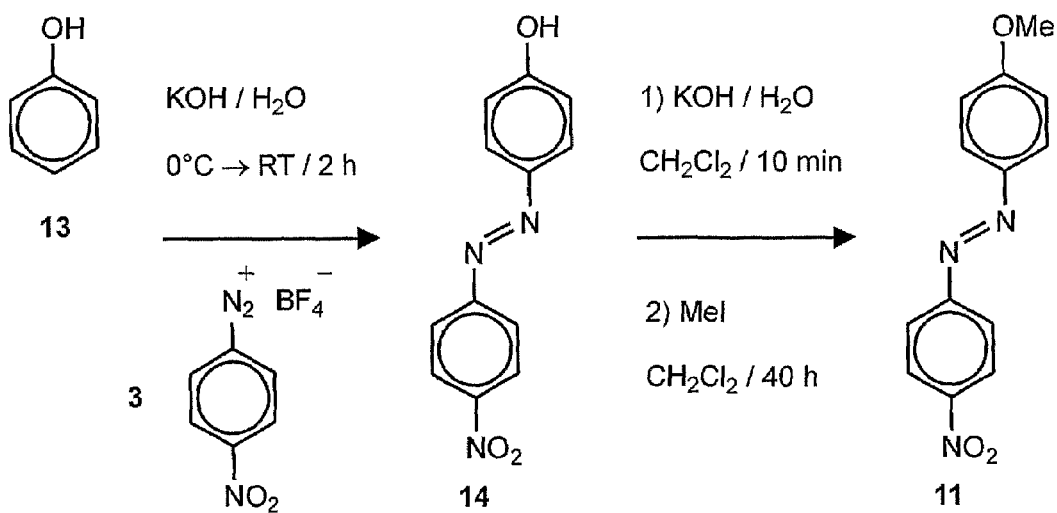
FIG. 25 is a schematic of the synthesis of the 4-nitrophenylazoanisole 11.

4-(4'-Nitrophenylazo)phenol (14). A solution of 3 (0.72 g, 3 mmol) in H$_2$O (15 mL) was added over a period of 30 min to a solution of 13 (0.29 g, 3 mmol) in aqueous KOH (0.3 M, 10 mL) and H$_2$O (5 mL) maintained at 0° C. (see FIG. 25). After warming up to ambient temperature, an additional portion of aqueous KOH (0.3 M, 5 mL) was added and the pH was maintained at about 8 for 100 min with additional aliquots of aqueous KOH (0.3 mL). The pH was lowered to about 2 with the addition of aqueous HCl (1 M), the mixture was cooled to 0° C., and maintained at this temperature for one hour. The resulting precipitate was filtered, dissolved in MeCO$_2$Et (50 mL), and dried (MgSO$_4$). The evaporation of the solvent under reduced pressure resulted in 14 (0.65 g, 88%) as an orange solid. mp=208° C.; FABMS: m/z=243 [M+H]$^+$; $^1$H-NMR (300 MHz, acetone-d$_6$): δ=6.92-6.96 (2H, m), 7.84-7.87 (2H, m), 7.98-8.01 (2H, m), 8.35-8.40 (2H, m); $^{13}$C-NMR (75 MHz, acetonitrile-d$_3$): δ=117.1, 124.0, 125.9, 126.7, 147.5, 149.5, 157.2, 162.5.

4-(4'-Nitrophenylazo)anisole (11). Aqueous KOH (0.3 M, 6 mL) was added to a solution of 14 (0.21 g, 1 mmol) in CH$_2$Cl$_2$ (50 mL). After stirring for 10 min, the precipitate was filtered, washed with cold H$_2$O (10 mL), and dried. The resulting solid was suspended in CH$_2$Cl$_2$ (50 mL) and MeI (150 μL, 2 mmol) was added (see FIG. 25). The mixture was heated for 40 h under reflux and Ar. After cooling to ambient temperature, the mixture was washed with water (20 mL). The organic layer was dried (MgSO$_4$) and the solvent was evaporated under reduced pressure. The residue was purified by column chromatography [SiO$_2$: hexanes/CH$_2$Cl$_2$ (1:1)] resulting in 11 (0.10 g, 52%) as an orange solid. mp=151° C.; FABMS: m/z=258 [M+H]$^+$; $^1$H-NMR (400 MHz, chloroform-d): δ=3.88 (3H, s), 6.99-7.01 (2H, m), 7.93-7.95 (4H, m), 8.30-8.33 (2H, m); $^{13}$C-NMR (100 MHz, CDCl$_3$): δ=55.9, 114.7, 123.3, 124.9, 125.8, 147.2, 148.5, 156.2, 163.5.

2-Hydroxymethyl-4-(4'-nitrophenylazo)phenol (4). A solution of 3 (1.12 g, 5 mmol) in H$_2$O (15 mL) was added over 90 min to a solution of 2 (535 mg, 4.3 mmol) in aqueous NaOH (1 M, 5 mL) and H$_2$O (10 mL) maintained at 0° C. The mixture was stirred for a further 45 min. During this time, the temperature was allowed to rise to ambient conditions and the pH was maintained at about 8 by adding aliquots of aqueous NaOH (1 M). After the addition of aqueous HCl (1 M, 5 mL). The mixture was cooled to −5° C. and maintained at this temperature for one hour. The resulting precipitate was filtered, dissolved in MeCO$_2$Et (50 mL), and dried (MgSO$_4$). After filtration, the solvent was evaporated under reduced pressure and resulted in 4 (1.13 g, 96%) as a bright-orange solid. mp=178-179° C.; FABMS: m/z=274 [M+H]$^+$; $^1$H-NMR (500 MHz, chloroform-d): δ=2.43 (1H, bs), 5.03 (2H, s), 7.05 (1H, d, 9 Hz), 7.73 (1H, d, 2 Hz), 7.85 (1H, dd, 2 and 9 Hz), 7.97 (2H, d, 9 Hz), 8.15 (1H, bs), 8.36 (2H, d, 9 Hz); $^{13}$C-NMR (100 MHz, chloroform-d): δ=60.4, 116.3, 123.3, 123.8, 125.6, 125.7, 130.4, 147.1, 149.1, 157.1, 160.4.

2-(4'-Nitrophenylazo)-5a,6,6-trimethyl-5a,6-dihydro-12H-indolo[2,1-b][1,3] benzooxazine (7a). A solution of PBr$_3$ in CH$_2$Cl$_2$ (1:20 v/v, 360 μL) was added over 20 min to a solution of 4 (117 mg, 0.4 mmol) in CH$_2$Cl$_2$ (25 mL) maintained at 0° C. under N$_2$. The mixture was stirred for a further 3 h. During this time, the temperature was allowed to rise to ambient conditions. At this point, 5 (345 μL, 2 mmol) was added and the mixture was stirred for a further one hour. After filtration over a plug of SiO$_2$, the solvent was evaporated under reduced pressure and the residue was purified by HPLC [semi-preparative, MeCN/H$_2$O (95:5 v/v)] to give 7a (73 mg, 41%) as an orange-red solid. HPLC [analytical, MeCN/H$_2$O (90:10)]: RT=4.1 min, PA=1.4, APP=310.4±1.3 nm; mp=156° C.; FABMS: m/z=415 [M+H]$^+$; $^1$H-NMR (500 MHz, chloroform-d): δ=1.25 (3H, s), 1.51 (3H, s), 1.61 (3H, s), 4.66 (2H, s), 6.59 (1H, d, 8 Hz), 6.80 (1H, d, 9 Hz), 6.82 (1H, t, 7 Hz), 7.08 (1H, td, 1 and 8 Hz), 7.13 (1H, dd, 1 and 7 Hz), 7.74 (1H, dd, 2 and 9 Hz), 7.80 (1H, d, 2 Hz), 7.96 (2H, d, 9 Hz), 8.37 (2H, d, 9 Hz); $^{13}$C-NMR (100 MHz, chloroform-d): δ=16.7, 19.1, 26.2, 40.5, 48.2, 103.8, 108.6, 118.8, 119.4, 120.4, 121.5, 122.4, 122.7, 123.3, 124.9, 127.7, 138.4, 146.4, 147.4, 148.6, 156.5, 158.1.

2-(4'-Nitrophenylazo)-5a-phenyl-6,6-dimethyl-5a,6-dihydro-12H-indolo[2,1-b][1,3]benzooxazine (8a). A solution of PBr$_3$ in MeCN (1:10 v/v, 190 µL) was added over 20 min to a solution of 4 (185 mg, 0.6 mmol) in MeCN (25 mL) maintained at 0° C. under Ar. After addition of Et$_3$N (80 µL), the mixture was stirred for a further one hour at 0° C. and then heated under reflux for 4 h. At this point, 6 (400 mg, 1.8 mmol) was added and the temperature was allowed to lower to ambient conditions. After 36 h, the solvent was evaporated under reduced pressure and the residue was purified by column chromatography [SiO$_2$, hexane/CH$_2$Cl$_2$ (1:1 v/v)] to give 8a (135 mg, 51%) as an orange-red solid. HPLC [analytical, MeCN/H$_2$O (90:10 v/v)]: RT=4.1 min, PA=1.6, APP=303.2±1.0 nm; mp=200° C.; FABMS: m/z=476 [M]$^+$; $^1$H-NMR (400 MHz, chloroform-d): δ=0.85 (3H, s), 1.60 (3H, s), 4.57 (1H, d, 11 Hz), 4.67 (1H, d, 11 Hz), 6.75 (1H, d, 8 Hz), 6.90 (1H, t, 7 Hz), 6.97 (1H, d, 9 Hz), 7.16-7.19 (2H, m), 7.35-7.42 (3H, m), 7.64-7.73 (4H, m), 7.93 (2H, d, 9 Hz), 8.34 (2H, d, 9 Hz); $^{13}$C-NMR (100 MHz, chloroform-d): δ=22.9, 31.8, 41.2, 49.8, 104.8, 109.2, 118.7, 120.6, 120.7, 122.4, 122.6, 123.3, 124.3, 124.9, 127.8, 128.3, 128.7, 129.0, 137.0, 138.0, 146.6, 147.5, 148.4, 156.2, 157.9.

X-Ray Crystallography. Single-crystals of 1d were grown from an equimolar solution of 1a and Bu$_4$CN in chloroform/hexane (2:1 v/v) maintained in the refrigerator. Single crystals of 7a and 8a were grown by vapor diffusion of MeOH into a solution of the corresponding compound in chloroform/hexane (2:3 v/v for 7a or 2:1 v/v for 8a).

Crystal data for 1d: [C$_{24}$H$_{20}$N$_3$O$_3$](C$_{16}$H$_{36}$N).3H$_2$O, M=694.94, monoclinic, P2$_1$/n (no. 14), a=9.5783(9), b=25.749(3), c=16.5586(17) Å, β=96.163(8)°, V=4060.3(7) Å$^3$, Z=4, D$_c$=1.137 g cm$^{-3}$, µ(Cu—Kα)=0.606 mm$^{-1}$, T=173K, yellow/brown needles; 7678 independent measured reflections, F$^2$ refinement, R$_1$=0.103, wR$_2$=0.159, 5514 independent observed absorption-corrected reflections [|F$_o$|>4σ(↑F$_o$|), 2θ$_{max}$=142° ], 468 parameters. CCDC 283555.

Crystal Data for 7a. C$_{24}$H$_{22}$N$_4$O$_3$, M=414.46, monoclinic, P2$_1$/c (no. 14), a=22.661(4), b=14.466° (18), c=13.077(6) Å, β=102.33(3)°, V=4188(2) Å$^3$, Z=8 (two independent molecules), D$_c$=1.315 g cm$^{-3}$, µ(Mo—Kα=0.089 mm$^1$, T=203 K, orange platy needles; 7353 independent measured reflections, F$^2$ refinement, R$_1$=0.064, wR$_2$=0.127, 3957 independent observed reflections [|F$_o$|>4σ(|F$_o$|), 2θ$_{max}$=50° ], 560 parameters. CCDC 261143.

Crystal Data for 8a. C$_{29}$H$_{24}$N$_4$O$_3$, M=476.52, monoclinic, P2$_1$/c (no. 14), a=8.7976(12), b=18.011(6), c=15.680(4) Å, βp=104.74(2)°, V=2402.7(10) Å$^3$, Z=4, D$_c$=1.317 g cm$^{-3}$, µ(Cu—Kα)=0.704 mm$^{-1}$, T=293 K, orange/yellow blocks; 3566 independent measured reflections, Bruker P4 diffractometer; F$^2$ refinement, R$_1$, =0.060, wR$_2$=0.168, 2719 independent observed reflections [|F$_o$|>4σ(|F$_o$|), 2θ$_{max}$=120° ], 314 parameters. CCDC 261144.

Absorption Spectroscopy. The steady-state spectra were recorded in aerated MeCN, using quartz cells with a path length of 0.5 cm. The transient spectra were recorded either in aerated MeCN, using quartz cells with a path length of 1.0 cm, or in polymethylmethacrylate (PMMA). The excitation source was a Nd-YAG laser (355 nm, 6 ns, 8 mJ). The PMMA films were prepared by spin-coating aliquots of CH$_2$Cl$_2$ solutions of the polymer (160 mg mL$^{-1}$) and 8a (8 mg mL$^{-1}$) on glass plates at 420 rpm for 9 s. The thicknesses of the resulting films (about 6 µm) was measured with a digital micrometer.

REFERENCES

1. Dunbar & Heintz (1997) *Prog. Inorg. Chem.* 45, 283-391.
2. Verdaguer et al. (1999) *Coord. Chem. Rev.* 192, 1023-1047.
3. Baraldo et al (2001) *Coord. Chem. Rev.* 219, 881-921.
4. Young et al. (2001) *Cyanide: Social, Industrial, and Economic Aspects*, Minerals, Metals, and Materials Society: Warrendale.
5. *Ullmann's Encyclopedia of Industrial Chemistry*, Wiley-VCH: New York, 2003.
6. Vennesland (1981) *Cyanide in Biology*, Academic Press: New York.
7. Kulig (1991) *Cyanide Toxicity*, U.S. Department of Health and Human Services: Atlanta.
8. Baskin & Brewer (1997) in *Medical Aspects of Chemical and Biological Warfare*, Sidell, et al., eds., TMM Publications: Washington, pp. 271-286.
9. Muir (1977) *Hazards in the Chemical Laboratory*, The Royal Chemical Society: London.
10. Baird & Cann (2005) *Environmental Chemistry*, Freeman: N.Y.
11. *Guidelines for Drinking-Water Quality* (1996) World Health Organization: Geneva.
12. Ikebukuro et al. (2000) in *Handbook of Water Analysis*, Nollet, ed., Marcel Dekker New York, vol. 102, pp. 367-385.
13. Desvergne & Czarnik, eds. (1997) *Chemosensors of Ion and Molecular Recognition*, Kluwer Academic Publishers: Dordrecht.
14. Ricco & Crooks, eds. (1998) *Acc. Chem. Res.* 31, 199-324.
15. Ellis & Walt, eds. (2000) *Chem. Rev.* 100, 2477-2738.
16. Fabbrizzi, ed. (2000) *Coord. Chem. Rev.* 205, 1-232.
17. Bianchi et al., eds. (1997) *Supramolecular Chemistry of Anions*, Wiley-VCH: New York.
18. Gale, ed. (2003) *Coord. Chem. Rev.* 240, 1-226.
19. (a) Schmidtchen et al. (1989) *Pure Appl. Chem.* 61, 1535-1546; (b) Schmidtchen & Berger (1997) *Chem. Rev.* 97, 1609-1646.
20. Dietrich (1993) *Pure Appl. Chem.* 65, 1457-1464.
21. Czarnik (1994) *Acc. Chem. Res.* 27, 302-308.
22. Atwood et al. (1996) *Chem. Commun.* 1996, 1401-1407.
23. (a) Scheerder et al. (1996) *Recl. Trav. Chim. Pays. Bas.* 115, 307-320; (b) Antonisse & Reinhoudt (1998) *Chem. Commun.* 1998, 443-448.
24. (a) Beer & Smith (1997) *Prog. Inorg. Chem.* 46, 1-96; (b) Beer (1998) *Acc. Chem. Res.* 31, 71-80; (c) Beer et al. (1999) *Coord. Chem. Rev.* 186, 3-36; (d) Beer & Gale (2001) *Angew. Chem. Intl. Ed.* 40, 487-516.
25. (a) de Silva et al. (1997) *Chem. Rev.* 97, 1515-1566. (b) de Silva et al. (1999) *Coord. Chem. Rev.* 186, 297-306.
26. (a) Gale et al., (1998) *Chem. Commun.* 1998, 1-8; (b) Sessler et al. (1998) *Pure Appl. Chem.* 70, 2401-2408; (c) Gale et al. (2001) *Coord. Chem. Rev.* 222, 57-102.
27. (a) Gale (2000) *Coord. Chem. Rev.* 199, 181-233; (b) Gale (2001) *Coord. Chem. Rev.* 213, 79-128.
28. (a) Wiskur et al. (2001) *Acc. Chem. Res.* 34, 963-972; (b) Lavigne & Anslyn (2001) *Angew. Chem. Intl. Ed.* 40, 3119-3130.
29. Amendola et al. (2001) *Coord. Chem. Rev.* 219, 821-837.
30. Martínez-Máñez & Sancerón (2003) *Chem. Rev.* 103, 4419-4476.
31. Suksai & Tuntulani (2003) *Chem. Soc. Rev.* 32, 192-202.
32. Miyaji & Sessler (2001) *Angew. Chem. Intl. Ed.* 40, 154-157
33. Kim & Hong (2002) *Chem. Commun.* 2002, 512-513.
34. (a) Ros-Lis et al. (2002) *Chem. Commun.* 2002, 2248-2249; (b) Jimenez et al. (2002) *Tetrahedron Lett.* 43, 2823-2825.
35. (a) Anzenbacher et al., (2002) *J. Am. Chem. Soc.* 124, 6232-6233; (b) Anzenbacher et al. (2004) *Tetrahedron* 60, 11163-11168.
36. Chow et al. (2004) *Inorg. Chem.* 43, 8387-8393.
37. (a) Badugu et al., (2004) *Anal. Chim. Acta* 522, 9-17; (b) Badugu et al. (2005) *Dyes Pigmen.* 64, 49-55; (c) Badugu et al., (2005) *J. Am. Chem. Soc.* 127, 3635-3641.
38. (a) Tomasulo et al., (2005) *Org. Lett.* 7, 1109-1112; (b) Tomasulo et al. (2005) *J. Org. Chem.* 70, 8180-8189.

39. Tomasulo & Raymo (2005) Org. Lett. 7, 4633-4636.

Patents, patent applications, books, and other publications cited herein are incorporated by reference in their entirety including Tomasulo et al. (J. Org. Chem. 71, 744-753, 2006) and supplementary information thereto.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim which recites "comprising" allows other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., arrangement of components in a product claim or order of steps in a method claim is not a limitation of the claim unless explicitly stated to be so). All combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A chromogenic compound, said compound being of the formula:

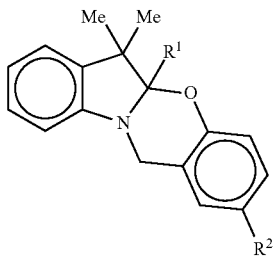

wherein $R^1$ is selected from the group consisting of alkyls, substituted alkyls, cycloalkyls, substituted cycloalkyls, aryls, and substituted aryls and $R^2$ is a chromophore selected from the group consisting of nitroso and azo dyes.

2. The compound according to claim 1, wherein $R^1$ is methyl.

3. The compound according to claim 1, wherein $R^2$ is nitrophenylazo.

4. The compound according to claim 1, which is 2-(4'-nitrophenylazo)-5a,6,6-trimethyl-5a,6-dihydro-12H-indolo[2,1-b][1,3]enzooxazine or 2-(4'-nitrophenylazo)-5a-phenyl-6,6-trimethyl-5a,6-dihydro-12H-indolo[2,1-b][1,3]benzooxazine.

5. A solution comprising at least one compound of claim 1 and a solvent, wherein said compound is soluble in the solution.

6. The solution according to claim 5, wherein said solvent is selected from the group consisting of aliphatic hydrocarbons, aromatic hydrocarbons, halogenated aliphatic hydrocarbons, and halogenated aromatic hydrocarbons.

7. The solution according to claim 5, which contains water.

8. A two-phase system, which is comprised of immiscible organic and aqueous phases, wherein said system further comprises one or more of the compounds of claim 1 and a phase-transfer catalyst.

9. The system according to claim 8, wherein said phase-transfer catalyst is selected from the group consisting of quaternary ammonium salts, phosphonium salts, crown ethers, and polyalkyleneglycols.

10. The system according to claim 8, wherein said organic phase is comprised of a solvent selected from the group consisting of aliphatic hydrocarbons, aromatic hydrocarbons, halogenated aliphatic hydrocarbons, and halogenated aromatic hydrocarbons.

11. The system according to claim 8, wherein said compound is soluble in said organic phase.

12. The system according to claim 8, wherein cyanide is dissolved at an alkaline pH in said aqueous phase.

13. A device, wherein said device comprises:
(a) a reaction cell, wherein a sample which might contain cyanide is contacted with at least one compound of claim 1, a solution comprising said at least one compound and a solvent, or a two-phase system comprising said at least one compound and immiscible organic and aqueous phases;
(b) a source of light transmitted to said reaction cell; and
(c) a detector of light received from said reaction cell.

14. The device according to claim 13 further comprising a network of fluid transfer lines which dispenses a first fixed amount of said compound, solution, or system into said reaction cell; dispenses a second fixed amount of said sample into said reaction cell; and empties said reaction cell in each reaction cycle.

15. A device, wherein said device comprises a support with a site for sample application and with the same or different site on which at least one compound of claim 1, a solution comprising said at least one compound and a solvent, or a two-phase system comprising said at least one compound and immiscible organic and aqueous phases is deposited thereon.

16. A method of synthesizing a compound, the method comprising: (a) reacting 2-hydroxymethylphenol and 4-nitrobenzenediazonium tetrafluoroborate in aqueous NaOH to produce 2-hydroxymethyl-4-(4'-nitrophenylazo)phenol and (b) brominating with phosphorus tribromide and reacting in situ with a 3,3'-dimethyl-3H-indole, which is substituted at the 2-position with $R^1$; thereby synthesizing said compound.

17. A method of detecting or quantifying cyanide, said method comprising:
(a) contacting a sample which might contain cyanide with at least one chromogenic compound according to claim 1, wherein cyanide cleaves chromogen to form chromophore;
(b) measuring light absorption by chromogen, chromophore, or both; and
(c) correlating a decrease in light absorption by chromogen, an increase in light absorption by chromophore, or both with the presence of cyanide such that it is detected or quantified.

18. The method of claim 17, wherein light absorption by chromogen is measured at one or more wavelengths from 360 nm to 400 nm.

19. The method of claim 17, wherein light absorption by chromophore is measured at one or more wavelengths from 560 nm to 600 nm.

20. The method of claim 17, wherein the difference between wavelengths for maximum light absorption by chromogen and chromophore is at least 200 nm.

21. The method of claim 17, wherein cyanide was concentrated in the sample prior to mixing.

22. The method of claim 17, wherein cyanide was diluted in the sample prior to mixing.

23. The method of claim 17, wherein immiscible organic and aqueous phases are mixed with a phase-transfer catalyst to cleave chromogen by cyanide to form chromophore.

24. The method of claim 17, wherein the ratio between light absorptions by chromogen and chromophore is calculated in a ratiometric assay.

25. The method of claim 17, wherein forming chromophore by cleavage of chromogen by cyanide is not significantly inhibited by 10 mM of halide anions.

26. The method of claim 17, which is sufficiently sensitive to detect or quantify 1 μM of cyanide anion.

27. A chromogenic compound, said compound being of the formula:

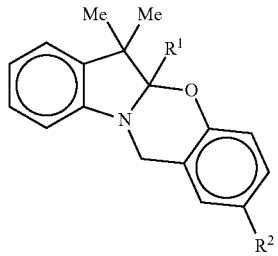

wherein $R^1$ is selected from the group consisting of alkyls and aryls, and $R^2$ is a chromophore selected from the group consisting of nitroso and azo dyes.

28. The compound according to claim 27, wherein $R^1$ is an alkyl and $R^2$ is an azo dye.

* * * * *